United States Patent
Lu

(10) Patent No.: US 11,847,798 B2
(45) Date of Patent: Dec. 19, 2023

(54) PIGMENT DETECTION METHOD AND ELECTRONIC DEVICE

(71) Applicant: HONOR DEVICE CO., LTD., Shenzhen (CN)

(72) Inventor: Henghui Lu, Beijing (CN)

(73) Assignee: HONOR DEVICE CO., LTD., Shenzhen (CN)

(*) Notice: Subject to any disclaimer, the term of this patent is extended or adjusted under 35 U.S.C. 154(b) by 233 days.

(21) Appl. No.: 17/259,626

(22) PCT Filed: Sep. 18, 2018

(86) PCT No.: PCT/CN2018/106216
§ 371 (c)(1),
(2) Date: Jan. 12, 2021

(87) PCT Pub. No.: WO2020/015142
PCT Pub. Date: Jan. 23, 2020

(65) Prior Publication Data
US 2021/0319589 A1    Oct. 14, 2021

(30) Foreign Application Priority Data
Jul. 16, 2018   (CN) .......................... 201810776213.1

(51) Int. Cl.
*G06T 7/90*     (2017.01)
*A61B 5/00*     (2006.01)

(52) U.S. Cl.
CPC ............... *G06T 7/90* (2017.01); *A61B 5/443* (2013.01); *G06T 2207/20028* (2013.01);
(Continued)

(58) Field of Classification Search
CPC ............ G06T 7/90; G06T 2207/20028; G06T 2207/20081; G06T 2207/20104;
(Continued)

(56) References Cited

U.S. PATENT DOCUMENTS

| | | |
|---|---|---|
| 10,055,844 B2 | 8/2018 | Hamada et al. |
| 10,130,297 B2 | 11/2018 | Schnidar et al. |

(Continued)

FOREIGN PATENT DOCUMENTS

| | | | | |
|---|---|---|---|---|
| CN | 101175537 A | * | 5/2008 | ......... A61F 13/0209 |
| CN | 101523169 A | | 9/2009 | |

(Continued)

OTHER PUBLICATIONS

Stefan Fischer et al., "Analysis of Skin Lesions With Pigmented Networks", published in 1996 IEEE (Year: 1996).*
(Continued)

*Primary Examiner* — Mekonen T Bekele
(74) *Attorney, Agent, or Firm* — RIMON P.C.

(57) ABSTRACT

A pigment detection method includes: extracting a first image from a to-be-detected RGB skin image, where the first image is used to represent a body reflection component in the RGB skin image, and the RGB skin image is photographed by a device having an RGB image photographing function; extracting a pigment from an R channel, a B channel, and a G channel of the first image based on a correspondence between a first spectral response curve of the pigment and a second spectral response curve of the device having the RGB image photographing function; and generating a pseudo-color image based on the extracted pigment, and displaying the pseudo-color image.

20 Claims, 13 Drawing Sheets

---

An electronic device extracts a first image from a to-be-detected RGB skin image — 301

The electronic device extracts a pigment from an R channel, a B channel, and a G channel of the first image based on a correspondence between a first spectral response curve of the pigment and a second spectral response curve of a device having an RGB image photographing function — 302

The electronic device generats a pseudo-color image based on the extracted pigment, and displaying the pseudo-color image — 303

(52) U.S. Cl.
CPC ............ *G06T 2207/20081* (2013.01); *G06T 2207/20104* (2013.01); *G06T 2207/30088* (2013.01)

(58) Field of Classification Search
CPC ......... G06T 2207/30088; G06T 11/001; A61B 5/443; A61B 2576/02; A61B 5/004; A61B 5/441; A61B 5/442; A61B 5/6898; A61B 5/742; A61B 5/7475; G16H 50/20; G16H 20/10
See application file for complete search history.

(56) References Cited

U.S. PATENT DOCUMENTS

| | | | |
|---|---|---|---|
| 10,182,757 B2 | 1/2019 | Gareau et al. | |
| 10,945,656 B2 | 3/2021 | Yaroslavsky et al. | |
| 11,317,851 B2 | 5/2022 | Kikuchi et al. | |
| 2004/0223063 A1* | 11/2004 | DeLuca | H04N 1/62 348/E5.038 |
| 2006/0092315 A1 | 5/2006 | Payonk et al. | |
| 2007/0161910 A1 | 7/2007 | Preece et al. | |
| 2010/0271470 A1 | 10/2010 | Rech | |
| 2011/0058072 A1 | 3/2011 | Wang et al. | |
| 2014/0177955 A1 | 6/2014 | Srinivasan et al. | |
| 2014/0304629 A1 | 10/2014 | Cummins et al. | |
| 2014/0323873 A1 | 10/2014 | Cummins et al. | |
| 2017/0270691 A1 | 9/2017 | Maltz et al. | |
| 2018/0101338 A1* | 4/2018 | Lin | G06F 3/1284 |

FOREIGN PATENT DOCUMENTS

| | | | | |
|---|---|---|---|---|
| CN | 104586355 A | * | 5/2015 | ........... A61B 5/0077 |
| CN | 104586355 A | | 5/2015 | |
| CN | 104978707 A | * | 10/2015 | |
| CN | 105377132 A | | 3/2016 | |
| CN | 105578953 A | | 5/2016 | |
| CN | 105844242 A | | 8/2016 | |
| CN | 105933607 A | | 9/2016 | |
| CN | 106127709 A | | 11/2016 | |
| CN | 106388781 A | | 2/2017 | |
| CN | 206132659 U | * | 4/2017 | |
| CN | 106846421 A | | 6/2017 | |
| CN | 107371013 A | | 11/2017 | |
| CN | 107835402 A | | 3/2019 | |
| JP | 2007159876 A | * | 6/2007 | |
| JP | 2013043017 A | | 3/2013 | |
| JP | 2015085039 A | | 5/2015 | |
| JP | 2016087271 A | | 5/2016 | |
| KR | 20150141988 A | * | 12/2015 | ............. A61B 5/441 |
| KR | 20170083066 A | * | 7/2017 | ............. A61B 5/443 |
| KR | 20170083066 A | | 7/2017 | |
| KR | 20170100717 A | * | 9/2017 | ... G06T 2207/30088 |
| KR | 20170100717 A | | 9/2017 | |
| WO | 2014165820 A1 | | 10/2014 | |
| WO | 2020015142 A1 | | 1/2020 | |

OTHER PUBLICATIONS

Fischer et al., "Analysis of Skin Lesions With Pigmented Networks", published in 1996 IEEE (Year: 1996).*

Izumi Nishidate:"Estimation of Melanin and Hemoglobin Using Spectral Reflectance Images; Image by the Wiener Estimation Method", <<Sensors>> ,dated 2013, total 14 pages.

* cited by examiner

PIGMENT DETECTION METHOD AND ELECTRONIC DEVICE

CROSS-REFERENCE TO RELATED APPLICATIONS

This application is a National Stage of International Application No. PCT/CN2018/106216, filed on Sep. 18, 2018, which claims priority to Chinese Patent Application No. 201810776213.1, filed on Jul. 16, 2018, both of which are hereby incorporated by reference in their entireties.

TECHNICAL FIELD

This application relates to the field of terminal technologies, and in particular, to a pigment detection method and an electronic device.

BACKGROUND

Skin pigment distribution is directly related to skin appearance and many skin problems. For example, uneven distribution of melanin leads to skin problems such as chloasma, freckles, and sunburn. For another example, a change in hemoglobin content is directly related to acne, sensitive skin, inflammation, and angiotelectasis. Therefore, accurate detection of skin pigment not only plays an important role in research and test of effectiveness of skin care products and skin care instruments, but also provides important guidance for consumers' daily beauty treatment and skin care.

Currently, skin pigment can be detected using an application on a mobile terminal. A common skin pigment detection manner includes: performing offline training by using skin images that feature different skin colors and that are acquired in different scenarios, to obtain a detection model used to separate a skin pigment; and performing detection on a test image using the detection model to separate a skin pigment. Because mobile detection scenarios vary greatly, it is impossible to acquire skin images in all scenarios for training. Therefore, the detection model is ill-suited to skin pigment detection performed in a scenario of complex variables. As a result, the prior art detection model has poor applicability.

SUMMARY

This application provides a pigment detection method and an electronic device, to resolve a problem of poor applicability of an existing skin pigment detection technology.

According to a first aspect, an embodiment of this application provides a pigment detection method. The method includes: extracting a first image from a to-be-detected RGB skin image, where the first image is used to represent a body reflection component in the RGB skin image, and the RGB skin image is photographed by a device having an RGB image photographing function; extracting a pigment from an R channel, a B channel, and a G channel of the first image based on a correspondence between a first spectral response curve of the pigment and a second spectral response curve of the device having the RGB image photographing function; and generating a pseudo-color image based on the extracted pigment, and displaying the pseudo-color image.

Based on this solution, the first image is extracted from the to-be-detected RGB skin image, where the first image is used to represent the body reflection component in the RGB skin image, and the RGB skin image is photographed by the device having the RGB image photographing function. Further, the pigment is extracted from the first image based on the relationship between the first spectral response curve of the pigment and the second spectral response curve of the device having the RGB image photographing function. In this way, pigment extraction is performed based on the spectral response relationship, so that pigments in RGB skin images photographed in different scenarios can be detected, avoiding a case in the prior art in which pigment detection can be performed only after training is performed in advance by using skin images acquired in different scenarios. Therefore, pigment detection based on this solution has relatively good applicability.

Further, to improve fidelity of the first image extracted from the RGB skin image, in a possible implementation, the to-be-detected RGB skin image is converted into a first Lab image; a body reflection component is extracted from each of an L channel, an a channel, and a b channel of the first Lab image; the body reflection components extracted from the L channel, the a channel, and the b channel of the first Lab image are combined to obtain a second Lab image; and the second Lab image is converted into an RGB image to obtain the first image.

In this manner, the body reflection components are extracted, so that color-related information (the a channel and the b channel) and color-unrelated information (the L channel) can be separated, to separately process the color-related information, thereby helping improve the fidelity of the first image.

In a possible design, the body reflection component of the L channel of the first Lab image is a difference between an initial value of the L channel of the first Lab image and a surface reflection component of the L channel of the first Lab image; the body reflection component of the a channel of the first Lab image is a difference between an initial value of the a channel of the first Lab image and a surface reflection component of the a channel of the first Lab image; the body reflection component of the b channel of the first Lab image is a difference between an initial value of the b channel of the first Lab image and a surface reflection component of the b channel of the first Lab image; and the surface reflection components of the L channel, the a channel, and the b channel of the first Lab image are obtained by separately performing filtering processing on the initial values of the L channel, the a channel, and the b channel of the first Lab image. According to this design, the surface reflection components of the L channel, the a channel, and the b channel can be filtered out, to accurately extract the body reflection components of the L channel, the a channel, and the b channel.

In a possible design, to improve pigment detection accuracy, the surface reflection components of the L channel, the a channel, and the b channel of the first Lab image may be obtained by separately performing bilateral filtering processing on the initial values of the L channel, the a channel, and the b channel of the first Lab image. This design can help further retain edge information of the first image, thereby improving the pigment detection accuracy.

In a possible design, the pigment includes but is not limited to any one of the following: hemoglobin, melanin, carotene, lipochrome, and bile pigment.

According to a second aspect, an embodiment of this application provides an electronic device, where the electronic device includes a memory, a processor, and a display screen. The memory is configured to store a program instruction. The processor is configured to read the program instruction stored in the memory, and perform the following operations: extracting a first image from a to-be-detected RGB skin image, where the first image is used to represent a body reflection component in the RGB skin image, and the RGB skin image is photographed by a device having an RGB image photographing function; extracting a pigment from an R channel, a B channel, and a G channel of the first image based on a correspondence between a first spectral response curve of the pigment and a second spectral response curve of the device having the RGB image photographing function; and generating a pseudo-color image based on the extracted pigment, and displaying the pseudo-color image. The display screen is configured to display the pseudo-color image.

In a possible design, the processor is specifically configured to perform the following operations: converting the to-be-detected RGB skin image into a first Lab image; extracting a body reflection component from each of an L channel, an a channel, and a b channel of the first Lab image; combining the body reflection components extracted from the L channel, the a channel, and the b channel of the first Lab image to obtain a second Lab image; and converting the second Lab image into an RGB image to obtain the first image.

In a possible design, the body reflection component of the L channel of the first Lab image is a difference between an initial value of the L channel of the first Lab image and a surface reflection component of the L channel of the first Lab image; the body reflection component of the a channel of the first Lab image is a difference between an initial value of the a channel of the first Lab image and a surface reflection component of the a channel of the first Lab image; the body reflection component of the b channel of the first Lab image is a difference between an initial value of the b channel of the first Lab image and a surface reflection component of the b channel of the first Lab image; and the surface reflection components of the L channel, the a channel, and the b channel of the first Lab image are obtained by separately performing filtering processing on the initial values of the L channel, the a channel, and the b channel of the first Lab image.

In a possible design, that the surface reflection components of the L channel, the a channel, and the b channel of the first Lab image are obtained by separately performing filtering processing on the initial values of the L channel, the a channel, and the b channel of the first Lab image includes: the surface reflection components of the L channel, the a channel, and the b channel of the first Lab image are obtained by separately performing bilateral filtering processing on the initial values of the L channel, the a channel, and the b channel of the first Lab image.

In a possible design, the pigment includes but is not limited to any one of the following: hemoglobin, melanin, carotene, lipochrome, and bile pigment.

According to a third aspect, an embodiment of this application provides a computer storage medium, where the computer storage medium stores a program instruction, and when the program instruction is run on an electronic device, the electronic device is enabled to perform the method according to any one of the first aspect in the embodiments of this application or the possible designs of the first aspect.

According to a fourth aspect, an embodiment of this application provides a computer program product. When the computer program product is run on an electronic device, the electronic device is enabled to perform the method according to any one of the first aspect in the embodiments of this application or the possible designs of the first aspect.

According to a fifth aspect, an embodiment of this application provides a chip, where the chip is coupled to a memory in an electronic device, and controls the electronic device to perform the method according to any one of the first aspect in the embodiments of this application or the possible designs of the first aspect.

In addition, for technical effects brought by the second aspect to the fifth aspect, refer to the description in the first aspect. Details are not described herein again.

It should be noted that the "coupling" in the embodiments of this application means that two components are directly or indirectly combined with each other.

DESCRIPTION OF EMBODIMENTS

The following further describes in detail the embodiments of this application with reference to accompanying drawings.

It should be understood that, in the embodiments of this application, "at least one" means one or more, and "a plurality of" means two or more. "and/or" describes an association relationship for describing associated objects and represents that three relationships may exist. For example, A and/or B may represent the following three cases: Only A exists, both A and B exist, and only B exists. A and B may be in a singular or plural form. The character "/" generally indicates an "or" relationship between the associated objects. "At least one (item) of the following" or a similar expression thereof means any combination of these items, including a single item or any combination of a plurality of items. For example, at least one (item) of a, b, or c may represent: a; b; c; a and b; a and c; b and c; or a, b, and c, where a, b, and c each may be in a singular or plural form.

The embodiments disclosed in this application may be applied to an electronic device.

In some embodiments of this application, the electronic device may be a portable electronic device including a function such as a personal digital assistant function and/or a music player function, for example, a mobile phone, a tablet computer, a wearable device (such as a smart watch) with a wireless communication function, or a vehiclemounted device. An example embodiment of a portable electronic device includes but is not limited to a portable electronic device using iOS®, Android®, Microsoft®, or another operating system. The foregoing portable electronic device may alternatively be a laptop computer (Laptop) having a touch-sensitive surface (for example, a touch panel), or the like. It should also be understood that, in some other embodiments of this application, the foregoing electronic device may alternatively be a desktop computer having a touch-sensitive surface (for example, a touch panel).

Figure 1:
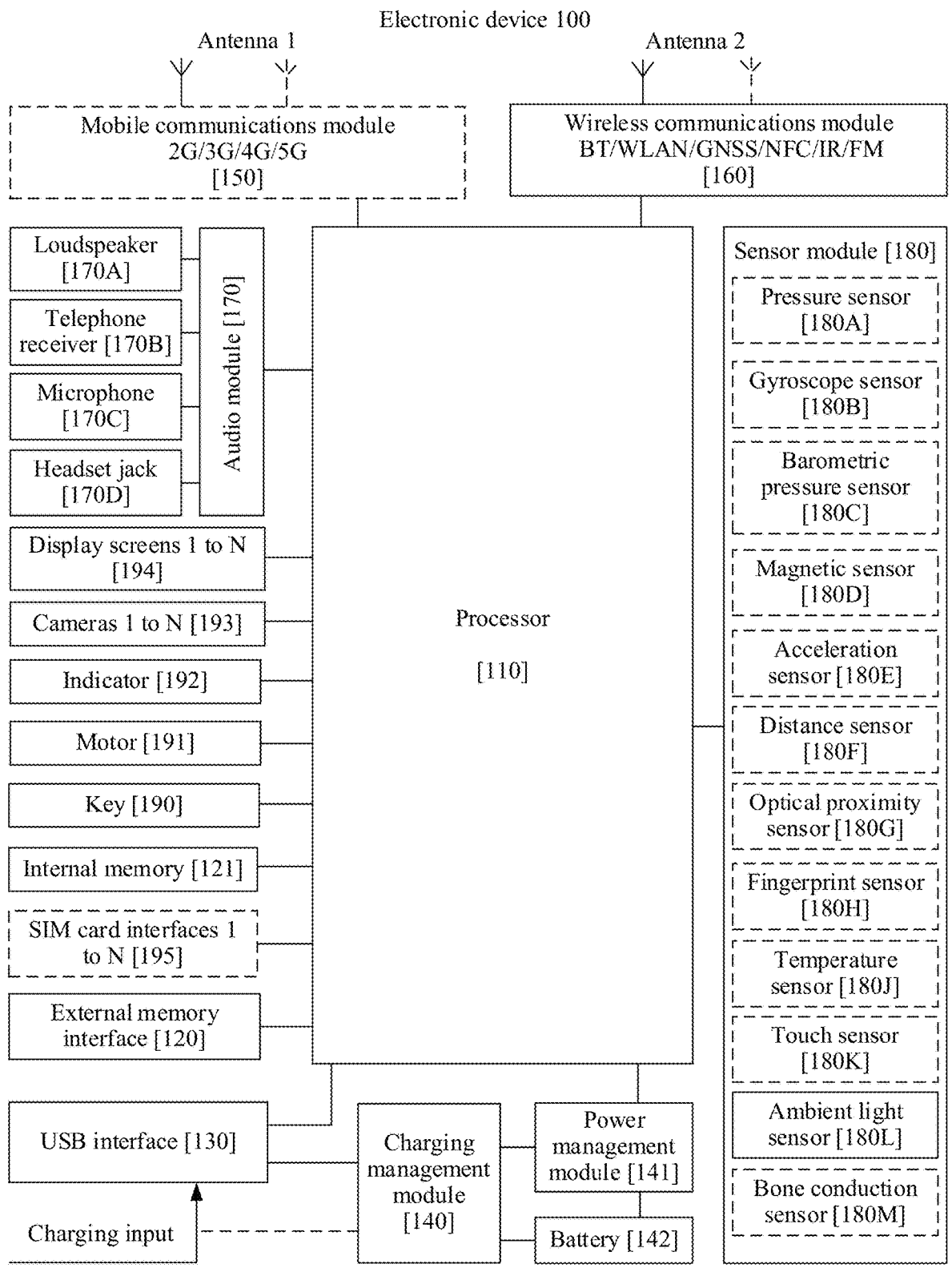
FIG. 1 is a schematic diagram of a structure of an electronic device to which an embodiment of this application is applicable.

FIG. 1 is an example of a schematic diagram of a structure of an electronic device.

The electronic device 100 may include a processor 110, an external memory interface 120, an internal memory 121, and a universal serial bus (universal serial bus, USB) interface 130, a charging management module 140, a power management module 141, a battery 142, an antenna 2, a wireless communications module 160, an audio module 170, a loudspeaker 170A, a telephone receiver 170B, a microphone 170C, a headset jack 170D, a sensor module 180, a key 190, a motor 191, an indicator 192, a camera 193, a display screen 194, and the like. The sensor module 180 includes an ambient light sensor 180L. In addition, the sensor module 180 may further include a pressure sensor 180A, a gyroscope sensor 180B, a barometric pressure sensor 180C, a magnetic sensor 180D, an acceleration sensor 180E, a distance sensor 180F, an optical proximity sensor 180G, a fingerprint sensor 180H, a temperature sensor 180J, a touch sensor 180K, a bone conduction sensor 180M, and the like.

In some other embodiments, the electronic device 100 in this embodiment of this application may further include an antenna 1, a mobile communications module 150, a subscriber identity module (subscriber identification module, SIM) card interface 195, and the like.

The processor 110 may include one or more processing units. For example, the processor 110 may include an application processor (AP), a modem processor, a graphics processing unit (GPU), an image signal processor (ISP), a controller, a memory, a video codec, a digital signal processor (DSP), a baseband processor, a neural-network processing unit (NPU), and/or the like. Different processing units may be independent devices, or may be integrated into one or more processors.

In some embodiments, a memory may further be disposed in the processor 110, and is configured to store an instruction and data. For example, the memory in the processor 110 may be a cache memory. The memory may store an instruction or data that is recently used or cyclically used by the processor 110. If the processor 110 needs to use the instruction or the data again, the processor 110 may directly invoke the instruction or the data from the memory. This avoids repeated access and reduces a waiting time of the processor 110, thereby improving system efficiency.

In some other embodiments, the processor 110 may further include one or more interfaces. For example, the interface may be the USB interface 130. For another example, the interface may alternatively be an inter-integrated circuit (I2C) interface, an inter-integrated circuit sound (I2S) interface, a pulse code modulation (PCM) interface, a universal asynchronous receiver/transmitter (UART) interface, a mobile industry processor interface (MIPI), a general purpose input/output (GPIO) interface, a SIM interface, or the like. It can be understood that in this embodiment of this application, different modules of the electronic device 100 may be connected through an interface, so that the electronic device 100 can implement different functions, for example, photographing and processing. It should be noted that a connection manner of the interface in the electronic device 100 is not limited in this embodiment of this application.

The USB interface 130 is an interface that complies with a USB standard specification. For example, the USB interface 130 may include a mini USB interface, a micro USB interface, a USB type C interface, and the like. The USB interface 130 may be configured to connect to a charger to charge the electronic device 100, may be configured to transmit data between the electronic device 100 and a peripheral device, or may be configured to connect to a headset and play audio by using the headset. The interface may further be configured to connect to another electronic device, for example, an augmented reality (AR) device.

The charging management module 140 is configured to receive a charging input from the charger. The charger may be a wireless charger, or may be a wired charger. In some embodiments of wired charging, the charging management module 140 may receive a charging input from a wired charger by using the USB interface 130. In some embodiments of wireless charging, the charging management module 140 may receive a wireless charging input by using a wireless charging coil of the electronic device 100. While charging the battery 142, the charging management module 140 may further supply power to the electronic device by using the power management module 141.

The power management module 141 is configured to connect to the battery 142, the charging management module 140, and the processor 110. The power management module 141 receives an input from the battery 142 and/or the charging management module 140, and supplies power to the processor 110, the internal memory 121, the external memory 121, the display screen 194, the camera 193, the wireless communications module 160, and the like. The power management module 141 may further be configured to monitor parameters such as a battery capacity, a quantity of battery cycles, and a battery health status (electric leakage and impedance). In some other embodiments, the power management module 141 may alternatively be disposed in the processor 110. In some other embodiments, the power management module 141 and the charging management module 140 may alternatively be disposed in a same device.

A wireless communication function of the electronic device 100 may be implemented by using the antenna 1, the antenna 2, the mobile communications module 150, the wireless communications module 160, the modem processor, the baseband processor, and the like.

The antenna 1 and the antenna 2 are configured to transmit and receive electromagnetic wave signals. Each antenna in the electronic device 100 may be configured to cover one or more communication frequency bands. Different antennas may further be multiplexed to improve antenna utilization. For example, the antenna 1 may be multiplexed as a wireless local area network diversity antenna. In some other embodiments, the antenna may be used in combination with a tuning switch.

The mobile communications module 150 may provide a wireless communication solution applied to the electronic device 100, including 2G, 3G, 4G, 5G, or the like. The mobile communications module 150 may include at least one filter, a switch, a power amplifier, a low noise amplifier (LNA), and the like. The mobile communications module 150 may receive an electromagnetic wave by using the antenna 1, perform processing such as filtering and amplification on the received electromagnetic wave, and transmit a processed electromagnetic wave to the modem processor for demodulation. The mobile communications module 150 may further amplify a signal modulated by the modem processor, convert the amplified signal into an electromagnetic wave by using the antenna 1, and radiate the electromagnetic wave through the antenna 1. In some embodiments, at least some function modules in the mobile communications module 150 may be disposed in the processor 110. In some embodiments, at least some function modules in the mobile communications module 150 and at least some modules in the processor 110 may be disposed in a same device.

The modem processor may include a modulator and a demodulator. The modulator is configured to modulate a to-be-sent low-frequency baseband signal into a medium-high-frequency signal. The demodulator is configured to demodulate a received electromagnetic wave signal into a low-frequency baseband signal. Then, the demodulator transmits the low-frequency baseband signal obtained through demodulation to the baseband processor for processing. After the low-frequency baseband signal is processed by the baseband processor, a processed low-frequency baseband signal is transmitted to the application processor. The application processor outputs a sound signal by using an audio device (which is not limited to the loudspeaker 170A and the telephone receiver 170B), or displays an image or a video by using the display screen 194. In some embodiments, the modem processor may be an independent device. In some other embodiments, the modem processor may be independent of the processor 110, and disposed in a same device as the mobile communications module 150 or another function module.

The wireless communications module 160 may provide wireless communication solutions that are applied to the electronic device 100, for example, wireless local area network (WLAN) (such as wireless fidelity (Wi-Fi) network), Bluetooth (BT), global navigation satellite system (GNSS), frequency modulation (FM), near field communication (NFC), and infrared (IR) technologies. The wireless communications module 160 may be one or more devices integrated into at least one communications processing module. The wireless communications module 160 receives an electromagnetic wave signal by using the antenna 2, performs frequency modulation and filtering processing on the electromagnetic wave signal, and sends a processed signal to the processor 110. The wireless communications module 160 may further receive a to-be-sent signal from the processor 110, perform frequency modulation and amplification on the signal, convert a processed signal into an electromagnetic wave by using the antenna 2, and radiate the electromagnetic wave through the antenna 2.

In some embodiments, the antenna 1 of the electronic device 100 is coupled to the mobile communications module 150, and the antenna 2 is coupled to the wireless communications module 160, so that the electronic device 100 may communicate with a network and another device by using a wireless communications technology. The wireless communications technology may include global system for mobile communications (GSM), general packet radio service (GPRS), code division multiple access (CDMA), wideband code division multiple access (WCDMA), time-division code division multiple access (TD-SCDMA), long term evolution (LTE), BT, GNSS, WLAN, NFC, FM, an IR technology, and/or the like. The GNSS may include a global positioning system (GPS), a global navigation satellite system (GLONASS), a beidou navigation satellite system (BDS), a quasi-zenith satellite system (QZSS), and/or a satellite based augmentation system (SBAS).

The electronic device 100 implements a display function by using the GPU, the display screen 194, the application processor, and the like. The GPU is a microprocessor for image processing, and is connected to the display screen 194 and the application processor. The GPU is configured to perform mathematical and geometric calculation, and is configured to perform graphics rendering. The processor 110 may include one or more GPUs, and executes a program instruction to generate or change display information.

The display screen 194 is configured to display an image, a video, and the like. The display screen 194 includes a display panel. The display panel may use a liquid crystal display (LCD), an organic light-emitting diode (OLED), an active-matrix organic light-emitting diode (AMOLED), a flexible light-emitting diode (FLED), a mini LED, a micro LED, a quantum dot light-emitting diode (QLED), and the like. In some embodiments, the electronic device 100 may include one or N display screens 194, where N is a positive integer greater than 1.

The electronic device 100 may implement a photographing function by using the ISP, the camera 193, the video codec, the GPU, the display screen 194, the application processor, and the like.

The ISP is configured to process data fed back by the camera 193. For example, during photographing, after a shutter is opened, light is transmitted to a photosensitive element of the camera through a lens, an optical signal is converted into an electrical signal, and the photosensitive element of the camera transmits the electrical signal to the ISP for processing, and converts the electrical signal into a visual image. The ISP may further perform algorithm-based optimization on noise, luminance, and a skin color of the image. The ISP may further optimize parameters such as exposure and color temperature of a photographing scenario. In some embodiments, the ISP may be disposed in the camera 193.

The camera 193 is configured to capture a static image or video. An optical image is generated for an object by using a lens and is projected onto the photosensitive element. The photosensitive element may be a charge coupled device (CCD) or a complementary metal-oxide-semiconductor (CMOS) phototransistor. The photosensitive element converts an optical signal into an electrical signal, and then transmits the electrical signal to the ISP, to convert the electrical signal into a digital image signal. The ISP outputs the digital image signal to the DSP for processing. The DSP converts the digital image signal into an image signal in a standard RGB or YUV format or the like. In some embodiments, the electronic device 100 may include one or N cameras 193, where N is a positive integer greater than 1.

The DSP is configured to process a digital signal. In addition to the digital image signal, the DSP may further process another digital signal. For example, when the electronic device 100 selects a frequency, the DSP is configured to perform Fourier transform on frequency energy, or the like.

The video codec is configured to compress or decompress a digital video. The electronic device 100 can support one or more types of video codecs. In this case, the electronic device 100 can play or record videos in a plurality of encoding formats, for example, a moving picture experts group (MPEG)-1 format, an MPEG-2 format, an MPEG-3 format, and an MPEG-4 format.

The NPU is a neural-network (neural-network, NN) computing processor. By using a biological neural network structure, for example, by using a mode of transmission between human brain neurons, the NPU can rapidly process input information, and can further perform continuous self-learning. Applications such as intelligent cognition of the electronic device 100, for example, image recognition, facial recognition, speech recognition, and text understanding, can be implemented by using the NPU.

The external memory interface 120 may be configured to connect to an external memory card (for example, a micro SD card), to extend a storage capability of the electronic device 100. The external memory card communicates with the processor 110 by using the external memory interface 120, to implement a data storage function, for example, storing a music file, a video file, or the like in the external memory card.

The internal memory 121 may be configured to store computer executable program code, where the executable program code includes an instruction. The processor 110 runs the instruction stored in the internal memory 121, to perform various function applications of the electronic device 100 and data processing. The internal memory 121 may include a program storage area and a data storage area. The program storage area may store an operating system, an application required by at least one function (for example, an audio playback function or an image playback function), and the like. The data storage area may store data (for example, audio data and a phone book) created during use of the electronic device 100, and the like. In addition, the internal memory 121 may include a high-speed random access memory, and may further include a nonvolatile memory, for example, at least one magnetic disk storage device, a flash memory device, and a universal flash storage (universal flash storage, UFS).

The electronic device 100 can implement an audio function, for example, music playback or recording, by using the audio module 170, the loudspeaker 170A, the telephone receiver 170B, the microphone 170C, the headset jack 170D, the application processor, and the like.

The audio module 170 is configured to convert digital audio information into an analog audio signal for output, and is also configured to convert an analog audio input into a digital audio signal. The audio module 170 may further be configured to encode and decode an audio signal. In some embodiments, the audio module 170 may be disposed in the processor 110, or some function modules of the audio module 170 are disposed in the processor 110.

The loudspeaker 170A, also referred to as a "speaker", is configured to convert an audio electrical signal into a sound signal. The electronic device 100 can be used for listening to music or answering a hands-free call by using the loudspeaker 170A.

The telephone receiver 170B, also referred to as an "earpiece", is configured to convert an audio electrical signal into a sound signal. When a call or voice information is received on the electronic device 100, voice can be heard by putting the telephone receiver 170B near a human ear.

The microphone 170C, also referred to as a "voice tube" or a "mike", is configured to convert a sound signal into an electrical signal. When making a call or sending voice information, a user can make a sound near the microphone 170C with the user's mouth to input a sound signal to the microphone 170C. At least one microphone 170C may be disposed in the electronic device 100. In some other embodiments, two microphones 170C may be disposed in the electronic device 100, and can further implement a noise reduction function in addition to sound signal acquisition. In some other embodiments, three, four, or more microphones 170 C may alternatively be disposed in the electronic device 100, to implement sound signal acquisition and noise reduction, further identify a sound source, and implement a directional recording function and the like.

The headset jack 170D is configured to connect to a wired headset. The headset jack 170D may be a USB interface 130, or may be a 3.5-mm open mobile electronic device platform (OMTP) standard interface, a cellular telecommunications industry association of the USA (CTIA) standard interface, or the like.

The pressure sensor 180A is configured to sense a pressure signal, and can convert the pressure signal into an electrical signal. In some embodiments, the pressure sensor 180A may be disposed on the display screen 194. There are many types of pressure sensors 180A, for example, a resistive pressure sensor, an inductive pressure sensor, and a capacitive pressure sensor. The capacitive pressure sensor may include at least two parallel plates including a conducting material. When force is applied to the pressure sensor 180A, capacitance between electrodes changes. The electronic device 100 determines pressure intensity based on the capacitance change. When a touch operation is performed on the display screen 194, the electronic device 100 detects a strength of the touch operation by using the pressure sensor 180A. The electronic device 100 may alternatively obtain a touch position through calculation based on a signal detected by the pressure sensor 180A. In some embodiments, touch operations that are performed in a same touch position but have different touch operation strengths may be corresponding to different operation instructions. For example, when a touch operation with a touch operation strength less than a first pressure threshold is performed on an icon of an SMS message application, an instruction for viewing a short message is executed. When a touch operation with a touch operation strength greater than or equal to the first pressure threshold is performed on the icon of the SMS message application, an instruction for creating a new short message is executed.

The gyroscope sensor 180B may be configured to determine a moving posture of the electronic device 100. In some embodiments, angular velocities of the electronic device 100 relative to three axes (that is, x, y, and z axes) may be determined by using the gyroscope sensor 180B. The gyroscope sensor 180B may be used for image stabilization during photographing. For example, when a shutter is pressed, the gyroscope sensor 180B detects an angle at which the electronic device 100 shakes, calculates, based on the angle, a distance for which a lens module needs to compensate, and allows a lens to offset the shake of the electronic device 100 through reverse movement, to implement image stabilization. The gyroscope sensor 180B may also be used for navigation and a motion sensing game scenario.

The barometric pressure sensor 180C is configured to measure atmospheric pressure. In some embodiments, the electronic device 100 calculates an altitude by using the atmospheric pressure measured by the barometric pressure sensor 180C, to assist positioning and navigation.

The magnetic sensor 180D includes a Hall effect sensor. The electronic device 100 may detect, by using the magnetic sensor 180D, whether a flip leather case is open or closed. In some embodiments, when the electronic device 100 is a flip phone, the electronic device 100 may detect, by using the magnetic sensor 180D, whether a flip cover is open or closed, and further set, based on a detected open/closed state of a leather case or a detected open/closed state of the flip cover, attributes such as auto-unlocking is implemented when the flip phone is flipped open.

The acceleration sensor 180E may detect magnitude of accelerations of the electronic device 100 in various directions (generally three axes); may detect magnitude and a direction of gravity when the electronic device 100 is still; and may further be configured to recognize a posture of the electronic device, and applied to screen switching between a landscape mode and a portrait mode, a pedometer, or another application.

The distance sensor 180F is configured to measure a distance. The electronic device 100 may measure a distance by using infrared or laser. In some embodiments, in a photographing scenario, the electronic device 100 may measure a distance by using the distance sensor 180F, to implement fast focusing.

The optical proximity sensor 180G may include, for example, a light emitting diode (LED) and an optical detector, for example, a photodiode. The light emitting diode may be an infrared light emitting diode. The electronic device 100 emits infrared light by using the light emitting diode. The electronic device 100 detects infrared reflected light from an object nearby by using a photodiode. When sufficient reflected light is detected, the electronic device 100 can determine that there is an object near the electronic device 100. When insufficient reflected light is detected, the electronic device 100 can determine that there is no object near the electronic device 100. By using the optical proximity sensor 180G, the electronic device 100 may detect that a user holds the electronic device 100 close to an ear during a call, to automatically turn off a screen for power saving. The optical proximity sensor 180G may also be used for automatic screen unlocking or locking in a leather case mode or a pocket mode.

The ambient light sensor 180L is configured to sense ambient light brightness. The electronic device 100 may adaptively adjust brightness of the display screen 194 based on the sensed ambient light brightness. The ambient light sensor 180L may also be configured to automatically adjust white balance during photographing. The ambient light sensor 180L may also cooperate with the optical proximity sensor 180G to detect whether the electronic device 100 is in a pocket, to prevent touch by mistake.

The fingerprint sensor 180H is configured to acquire a fingerprint. By using a feature of the acquired fingerprint, the electronic device 100 can implement unlocking via the fingerprint, access an application lock, perform photographing via the fingerprint, answer a call via the fingerprint, and the like.

The temperature sensor 180J is configured to detect temperature. In some embodiments, the electronic device 100 executes a temperature processing policy by using the temperature detected by the temperature sensor 180J. For example, when the temperature reported by the temperature sensor 1807 exceeds a threshold, the electronic device 100 reduces performance of a processor located nearby the temperature sensor 1807, to reduce power consumption to implement thermal protection. In some other embodiments, when the temperature is less than another threshold, the electronic device 100 heats the battery 142 to prevent abnormal power-off of the electronic device 100 resulted from low temperature. In some other embodiments, when the temperature is less than still another threshold, the electronic device 100 increases an output voltage of the battery 142 to prevent abnormal power-off resulted from low temperature.

The touch sensor 180K is also referred to as a "touch panel". The touch sensor 180K may be disposed in the display screen 194, and the touch sensor 180K and the display screen 194 constitute a touchscreen, which is also referred to as a "touch control screen". The touch sensor 180K is configured to detect a touch operation performed on or near the touch sensor 180K. The touch sensor may transmit the detected touch operation to the application processor to determine a type of a touch event. A visual output related to the touch operation may be provided by using the display screen 194. In some other embodiments, the touch sensor 180K may alternatively be disposed in a position, different from a position of the display screen 194, on a surface of the electronic device 100.

The bone conduction sensor 180M may obtain a vibration signal. In some embodiments, the bone conduction sensor 180M may obtain a vibration signal of a vibrating bone block of a vocal-cord part of a human body. The bone conduction sensor 180M may also be in contact with pulses of a human body to receive blood pressure fluctuating signals. In some embodiments, the bone conduction sensor 180M may also be disposed in a headset, to combine with the headset into a bone conduction headset. The audio module 170 may obtain a voice signal by parsing the vibration signal of the vibrating bone block of the vocal-cord part obtained by the bone conduction sensor 180M, to implement a voice function. The application processor may obtain heart rate information by parsing the blood pressure fluctuating signals obtained by the bone conduction sensor 180M, to implement a heart rate detection function.

The key 190 may include a power key, a volume key, and the like. The key 190 may be a mechanical key, or may be a touch key. The electronic device 100 may receive a key input, and generate a key signal input related to a user setting and function control of the electronic device 100.

The motor 191 may generate a vibration alert. The motor 191 may be configured to provide an incoming-call vibration alert and a touch vibration feedback. For example, touch operations performed on different applications (for example, photographing and audio playback) may be corresponding to different vibration feedback effects. The motor 191 may also be corresponding to different vibration feedback effects for touch operations performed in different areas of the display screen 194. Different application scenarios (for example, time reminding, information receiving, an alarm clock application, and a game application) may also be corresponding to different vibration feedback effects. The touch vibration feedback effect may also be user-defined.

The indicator 192 may be an indicator light, and may be configured to indicate a charging status and a battery level change, or may be configured to indicate a message, a missed call, a notification, or the like.

The SIM card interface 195 is configured to connect to a SIM card. The SIM card may be inserted into the SIM card interface 195 or removed from the SIM card interface 195, to be in contact with or be separated from the electronic device 100. The electronic device 100 can support one or N SIM card interfaces, where N is a positive integer greater than 1. The SIM card interface 195 can support a nano-SIM card, a micro-SIM card, a SIM card, and the like. A plurality of cards may be inserted into a same SIM card interface 195 at the same time. The plurality of cards may be of a same type or different types. The SIM card interface 195 may also be compatible with different types of SIM cards. The SIM card interface 195 may also be compatible with an external memory card. The electronic device 100 interacts with a network by using a SIM card, to implement a call function, a data communication function, and the like. In some embodiments, the electronic device 100 uses an eSIM, that is, an embedded SIM card. The eSIM card may be embedded in the electronic device 100 and cannot be separated from the electronic device 100.

It can be understood that the schematic structure in this embodiment of this application does not constitute any specific limitation on the electronic device 100. In some other embodiments of this application, the electronic device 100 may include components more or fewer than those shown in the figure, or some components may be combined, some components may be split, or there may be a different component arrangement. The components shown in the figure may be implemented by hardware, software, or a combination of software and hardware.

The following describes this embodiment of this application in detail by using the electronic device 100 as an example.

In addition, it should be understood that applications supported by the electronic device in this embodiment of this application may include a photographing application, for example, a camera. In addition, the applications supported by the electronic device may further include a plurality of other applications, for example, drawing, gaming, phone, video player, music player, photo management, browser, calendar, and clock.

Figure 2:
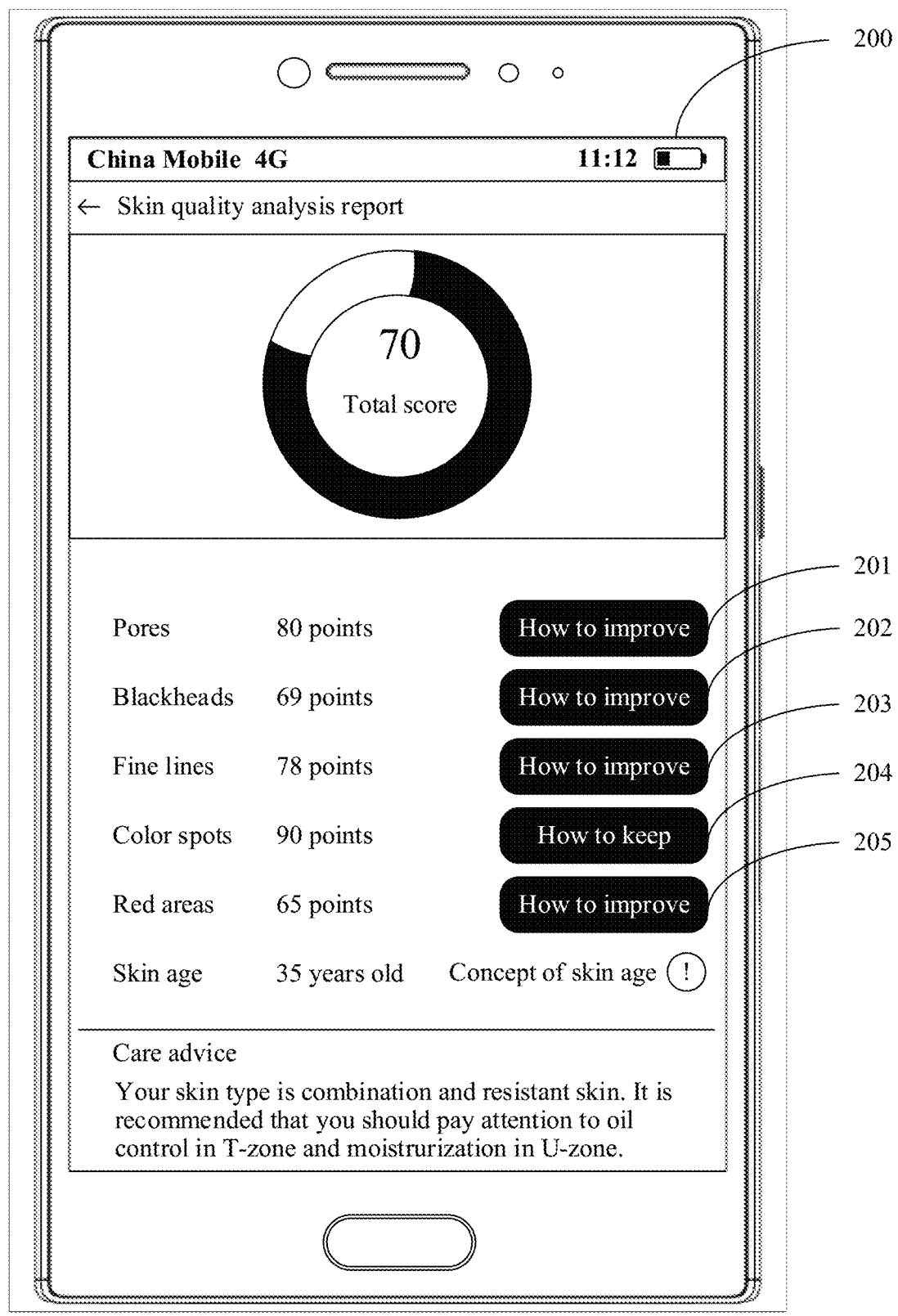
FIG. 2 is a schematic diagram of a user interface according to an embodiment of this application.

The applications supported by the electronic device in this embodiment of this application may further include an application for skin test. The application for skin test is to detect a facial skin features (for example, wrinkles, pores, blackheads, color spots, or a red area of facial skin) of a user by using a photographed facial image, and may provide a detection result report for the user. For example, the detection result report may include, but is not limited to, a score for each feature of the facial skin and comprehensive analysis on the facial skin, and may further display the facial image of the user, and mark a corresponding problem on the facial image based on a detection result of each feature. For example, blackheads are marked in a nose area, wrinkles are marked in a forehead area, and color spots are marked in a cheek area. It can be understood that the detection result report may be presented to the user on a user interface. For example, the detection result report may be presented on the user interface 200 shown in FIG. 2, and includes a comprehensive score, a skin age, and scores for pores, blackheads, fine lines, color spots, and a red area. In some other embodiments, the user interface 200 may further include a virtual button 201, a virtual button 202, a virtual button 203, a virtual button 204, and a virtual button 205. Using the virtual button 201 as an example, in response to an operation performed on the virtual button 201, the electronic device 100 displays a specific care advice for the pores on the display screen 194. For functions of the virtual button 202, the virtual button 203, the virtual button 204, and the virtual button 205, refer to a function of the virtual button 201. Details are not described herein again.

To make the electronic device more accurately detect the facial skin of the user, for example, in the user skin test solution in this embodiment of this application, a photographing condition detection module, an image quality detection module, and a region of interest (ROI) detection module, a skin feature detection module, a result analysis module, and the like may be integrated into the processor 110. In some embodiments, the photographing condition detection module, the image quality detection module, and the region of interest (ROI) detection module, the skin feature detection module, the result analysis module, and the like may be integrated into the application processor in the processor 110. In some other embodiments, an artificial intelligence (AI) chip is integrated into the processor 110, and the photographing condition detection module, the image quality detection module, and the region of interest (ROI) detection module, the skin feature detection module, the result analysis module, and the like are integrated into the AI chip, to implement user skin test.

The photographing condition detection module may detect a current photographing condition, to guide a user to perform photographing in a required photographing condition, to ensure that a photographed image meets a requirement, thereby ensuring accuracy of skin test performed based on the image. For example, the required photographing condition includes: ambient light is sufficient; there is an appropriate distance (for example, approximately 25 cm) between a human face and the electronic device; a face is straight; eyes are closed; no glasses are worn; a forehead is not covered by bangs as far as possible; focusing is accurate; there is no obvious shake; and the like.

After the photographing condition detection module performs detection successfully, the processor 110 enables intelligent light compensation. For example, when a current photographing condition meets a requirement, the photographing condition detection module determines that the detection succeeds. Specifically, in this embodiment of this application, the electronic device may use different light compensation modes (for example, a flash lamp mode or a flashlight mode) to perform light compensation for a face of a user, to meet requirements of detecting different facial skin features. After performing light compensation for the face of the user, the processor 110 may control the camera 193 to photograph the face of the user to obtain a facial image of the face of the user.

The image quality detection module may detect quality of the facial image, to ensure that the photographed image meets the requirements of detecting different facial skin features.

After the image quality detection module finds that the image quality meets the requirements, the ROI detection module may determine a to-be-detected ROI from the facial image. For example, an ROI of blackheads is a small area on a nose.

The skin feature detection module may detect each of facial skin features in the determined ROI, for example, detect wrinkles, pores, blackheads, color spots, a red area, and a degree of oiliness on the skin.

The result analysis module may analyze a detection result of the facial skin features detected by the skin feature detection module, and provide a score, a score ranking, and the like of each detection item for each skin feature.

In addition, in some embodiments, an image preprocessing module may further be integrated into the processor 110. The image preprocessing module may perform compression, cropping, and the like on the photographed facial image, so that the ROI detection module, the skin feature detection module, and the like perform subsequent processing.

To output a facial image analysis result, output a score of each detection item, or the like, the processor 110 may further display a detection report (including areas with a detection result of each feature in the facial image, for example, a nose area marked with blackheads, a forehead area marked with wrinkles, a cheek area marked with color spots; scores of all detection items; and the like) obtained through detection on the display screen 194 for the user to view, thereby improving user experience.

The following describes the embodiments of this application in detail with reference to the structure of the electronic device shown in FIG. 1.

To adapt to changes of a plurality of detection scenarios and resolve a problem of poor applicability of an existing skin pigment detection technology, an embodiment of this application provides a pigment detection method. In this method, the electronic device 100 can extract a pigment from an RGB skin image. Because a skin pigment (for example, melanin or hemoglobin) has a specific absorption spectrum, after a body reflection component is extracted from the skin image, the pigment can be separated from the body reflection component by using a spectrum analysis technology. Therefore, relatively good applicability can be achieved by using the pigment detection method for pigment detection.

The pigment detection method provided in this embodiment of this application may be applied to an application that is used for skin test and that is supported by the electronic device 100. For example, as shown in FIG. 5A to FIG. 5D, the display screen 194 of the electronic device 100 displays an icon 500 of an application for skin test. If finding an operation performed on the icon 500 (for example, the electronic device finds that a user taps the icon 500), in response to the operation performed on the icon 500, the electronic device 100 displays a user interface 510 of the application for skin test on the display screen 194. The user interface 510 of the application for skin test includes a virtual button 511 (during implementation, the virtual button may be named as "test", "take a photo", or the like). If finding an operation performed on the virtual button 511 (for example, the electronic device finds that the user taps the virtual button 511), in response to the operation performed on the virtual button 511, the electronic device 100 performs, according to the pigment detection method provided in this embodiment of this application, pigment detection on an area that is in an RGB skin image and in which a pigment needs to be detected.

The RGB skin image may be obtained by the electronic device 100 in response to the operation on the virtual button 511 by photographing a face of the user by using the camera 193. The camera 193 herein may be a front-facing camera or a rear-facing camera of the electronic device 100. Alternatively, the RGB skin image may be an image that is read, by the electronic device 100 in response to the operation on the virtual button 511, from the internal memory 121 or from an external memory by using the external memory interface 120. In this case, the RGB skin image may be an RGB skin image that is photographed in advance and that is stored in the internal memory 121 or the external memory.

For example, the RGB skin image may be an image obtained by the electronic device by photographing the face of the user by using the camera 193 (the camera 193 herein may be a front-facing camera or a rear-facing camera). After photographing, the electronic device 100 stores the obtained RGB skin image in the internal memory 121, and after finding the operation performed on the virtual button 511, the electronic device 100 may read the RGB skin image from the internal memory 121. In addition, during implementation, an RGB skin image stored in the internal memory 121 may alternatively be an image received by the electronic device 100 by using the mobile communications module 150 and/or the wireless communications module 160.

Further, after the electronic device 100 finds the operation performed on the virtual button 511, the user may alternatively choose whether the electronic device 100 performs photographing by using the camera 193 to obtain an RGB skin image or the electronic device 100 reads an RGB skin image from the internal memory 121 or the external memory. For example, after the electronic device 100 finds the operation performed on the virtual button 511, the display screen 194 displays a photo selection area 512. The photo selection area 512 may include prompt information such as "provide a photo" and "obtain a photo from", to remind the user to select a source of the RGB skin image, and the photo selection area 512 may further include a plurality of virtual buttons. Operations corresponding to the virtual buttons are performed based on operations performed on the virtual buttons by the user, to obtain RGB skin images in different ways. For example, the virtual button may be a first button 513 (a name of the first button 513 may be "camera", "take a photo", or the like) that represents obtaining an RGB skin image in a photographing manner; or the virtual button may be a second button 514 (a name of the second button 514 may be "storage", "album", or the like) that represents obtaining an RGB skin image by reading from a memory. After finding an operation performed by the user on the first button 513, in response to the operation performed by the user on the first button 513, the electronic device 100 may photograph a facial image of the user by using the camera 193, and use the facial image as an RGB skin image. After finding an operation performed by the user on the second button 514, the electronic device 100 may continue to remind the user to select an RGB skin image storage path, and read, from the storage path selected by the user, an image selected by the user as an RGB skin image. The storage path may be a default storage path of an "album" of the electronic device 100. The storage path may include a storage path of the internal memory 121, or may include a storage path of the external memory. In addition, it should be understood that the display of the photo selection area 512 may alternatively be triggered in a manner other than finding, by the electronic device 100, the operation performed on the virtual button 511. For example, a new virtual function button may be disposed on the user interface 510, to display the photo selection area 512 after the electronic device 100 finds an operation performed on the new virtual function button.

After the RGB skin image of the user is obtained by using the foregoing method, the display screen 194 may display an RGB skin image preview interface 520, and display the RGB skin image in a preview area 521 of the RGB skin image preview interface 520. The electronic device 100 may determine an ROI for pigment detection based on the RGB skin image in the preview area 521. For example, the electronic device 100 may automatically select an ROI through positioning analysis based on a facial feature point in the RGB skin image; the user may manually draw an ROI; or the electronic device 100 may provide an area, and the user may manually adjust the area provided by the electronic device 100 to obtain an ROI. Then, the ROI is used as an area that is in the RGB skin image and in which a pigment needs to be detected, and is used to perform pigment detection by using the pigment detection method provided in this embodiment of this application.

The following describes in detail how the processor 110 in the electronic device 100 specifically implements pigment detection on RGB skin images based on the RGB skin images obtained in the foregoing different manners. For a specific method, refer to a schematic flowchart shown in FIG. 3. The method includes the following steps.

Step 301. The processor 110 extracts a first image from a to-be-detected RGB skin image.

The first image is used to represent a body reflection component in the RGB skin image, and the RGB skin image is photographed by a device having an RGB image photographing function.

Herein, the RGB skin image may be a skin image of a to-be-detected part, for example, a facial image or a nose area image.

The RGB skin image is obtained by imaging after incident light is reflected through epidermis and absorbed and scattered by the epidermis, dermis, and subcutaneous tissues. The RGB skin image mainly includes two components: a surface reflection component and a body reflection component.

The surface reflection component is obtained by using energy that bounces back in a manner similar to mirror reflection when the incident light is incident on a skin surface, and may be used to analyze a topology feature of the skin surface, for example, wrinkles, pores, blackheads, and a skin texture.

The body reflection component is obtained by using energy that is returned after energy of the incident light enters skin and is absorbed and scattered by pigments, collagen, and the like in the epidermis and the dermis, and may be used to analyze optical properties of the subcutaneous tissues, for example, distribution of pigments such as melanin and hemoglobin. For example, the body reflection component may be extracted from the to-be-detected RGB skin image, to obtain the first image.

The device having the RGB image photographing function may be the electronic device 100, or may be a device connected to the electronic device 100, or may be a device not directly connected to the electronic device 100. In an example, the indirect connection may be a wireless connection, or may be a connection implemented by using another device, to send or transmit, to the electronic device 100, the RGB skin image photographed by the device having the RGB image photographing function. For example, the device having the RGB image photographing function is the electronic device 100. The RGB image photographing function is implemented by a camera 193 on the electronic device 100. For example, the camera 193 acquires the RGB skin image. For example, when an image needs to be acquired, an operation may be performed on a camera application installed in the electronic device 100, to enable the camera 193 by using the electronic device 100 to photograph an image. The camera application may be an application pre-installed in the electronic device 100 at delivery, or may be an application downloaded by a user. It should be noted that the RGB skin image may be an image pre-stored in the electronic device 100, or may be obtained through in real-time photographing by enabling the camera 193 by the electronic device 100.

Figure 4A:
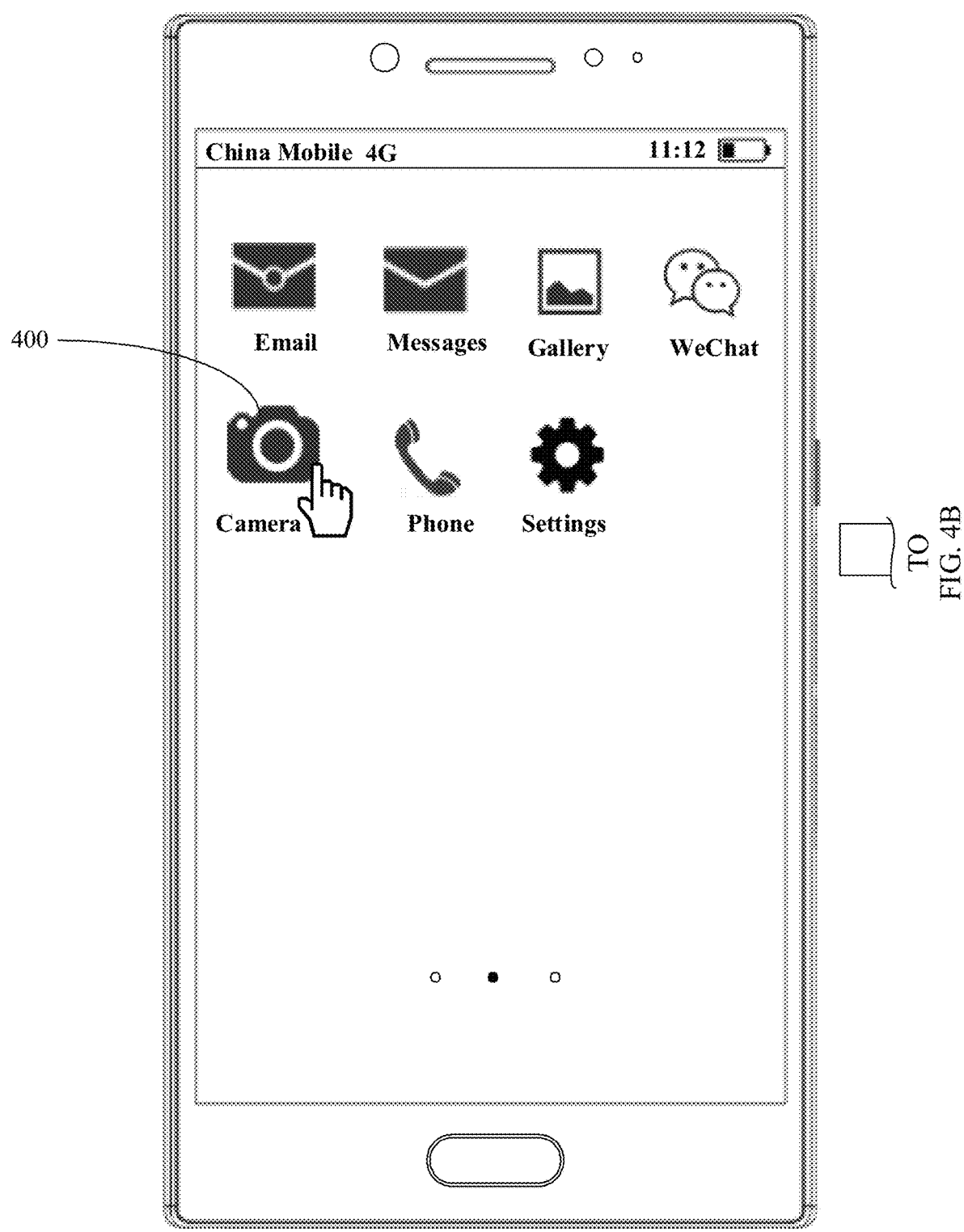
FIG. 4A and FIG. 4B are a schematic diagram of a user interface according to an embodiment of this application.
Figure 4B:
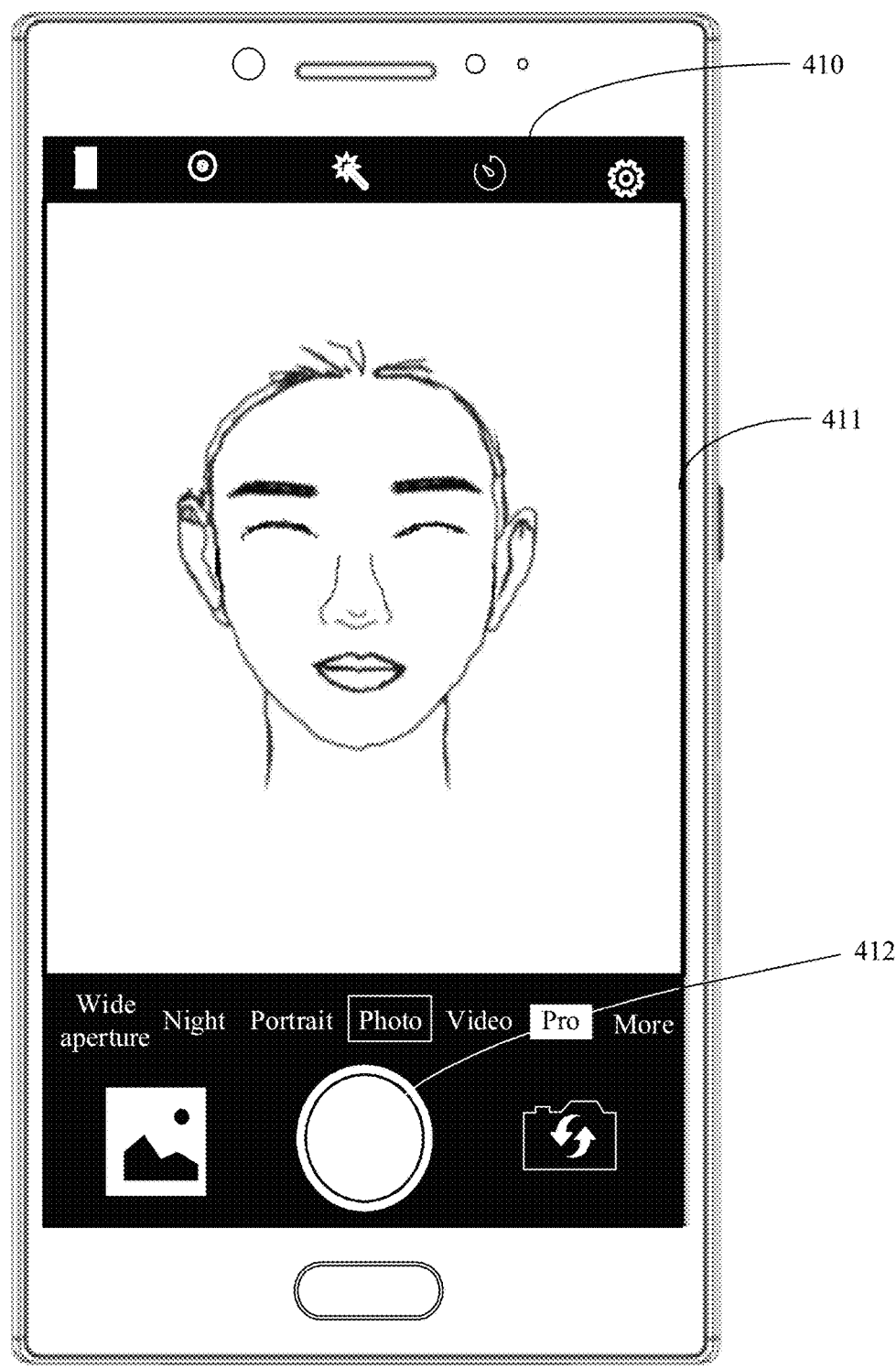

In a specific example, as shown in FIG. 4A and FIG. 4B, a display screen 194 of the electronic device 100 displays a home screen. The home screen includes an icon 400 of a camera application. In addition, the home screen may further include an email icon, an SMS message icon, a gallery icon, a WeChat icon, and the like. When an image needs to be photographed, the display screen 194 of the electronic device 100 may respond to an operation performed on the icon 400, for example, a touch operation performed on the icon 400. The display screen 194 displays a preview interface 410, and the preview interface 410 includes a preview area 411. The preview area 411 may be used to display the RGB skin image acquired by the camera 193. Using photographing of a facial image as an example, when the to-be-photographed image is displayed in the preview area 411, a touch operation may be performed on a virtual button 412, to acquire an RGB skin image.

In another specific example, the electronic device 100 may further include an application for skin test. As shown in FIG. 5A to FIG. 5D, the display screen 194 of the electronic device 100 displays the icon 500 of the application for skin test. In response to an operation performed on the icon 500, the electronic device 100 displays the user interface 510 of the application for skin test on the display screen 194. The user interface 510 includes the virtual button 511. If the electronic device 100 finds an operation performed on the virtual button 511, in response to the operation performed on the virtual button 511, the display screen 194 displays a preview interface 520 of a camera application, where the preview interface 520 includes a preview area 521. The preview area 521 is used to display the RGB skin image acquired by the camera 193.

Step 302. The processor 110 extracts a pigment from an R channel, a B channel, and a G channel of the first image based on a correspondence between a first spectral response curve of the pigment and a second spectral response curve of the device having the RGB image photographing function.

The pigment may include but is not limited to any one of the following: hemoglobin, melanin, carotene, lipochrome, and bile pigment.

Specifically, the processor 110 extracts the pigment from the R channel, the B channel, and the G channel of the first image based on the correspondence between the first spectral response curve of the pigment and the second spectral response curve of the device having the RGB image photographing function, and channel values of the three channels, namely the R channel, the G channel, and the B channel, of the first image.

Figure 6:
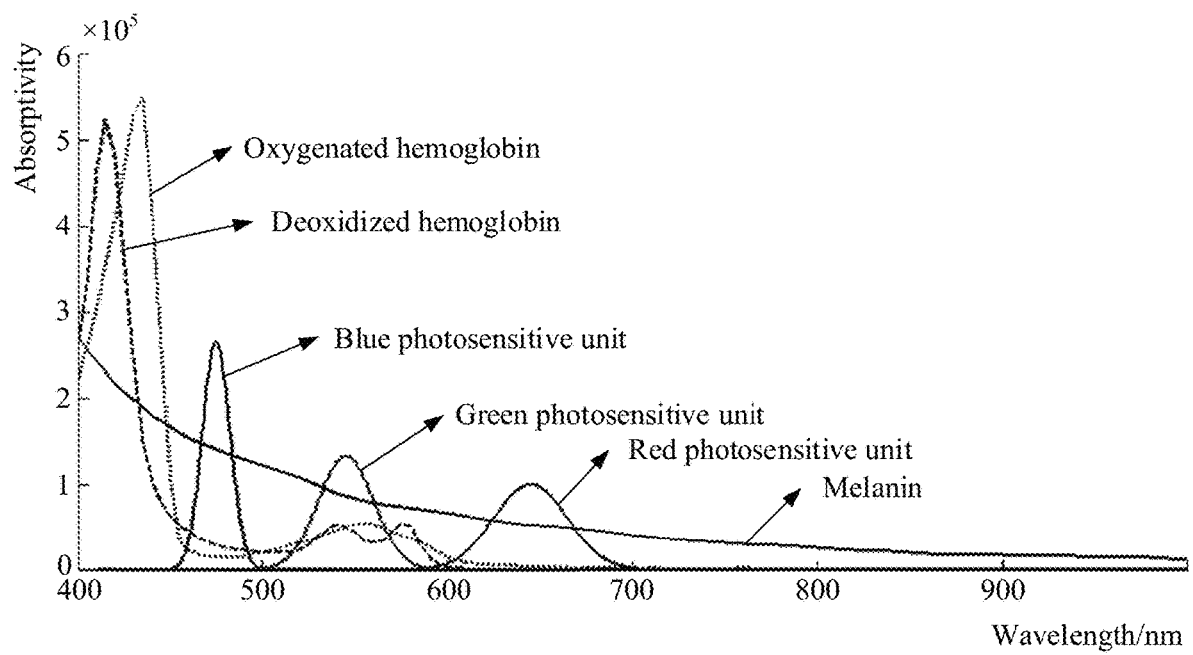
FIG. 6 is a schematic diagram of a spectral response curve according to an embodiment of this application.

For example, the first spectral response curve of the pigment reflects absorption values of the pigment in spectral segments of different wavelengths, for example, an absorption spectrum curve of melanin, an absorption spectrum curve of oxyhemoglobin, and an absorption spectrum curve of deoxyhemoglobin that are shown in FIG. 6. The second spectral response curve of the device having the RGB image photographing function reflects absorption values, corresponding to different spectral segments, of different photosensitive units in the device having the RGB image photographing function, for example, an absorption spectrum curve of a red (R) photosensitive unit, an absorption spectrum curve of a green (G) photosensitive unit, and an absorption spectrum curve of a blue (B) photosensitive unit that are shown in FIG. 6.

In a specific example, melanin and hemoglobin are extracted from the first image. Because the melanin and the hemoglobin have specific absorption spectra, the melanin and the hemoglobin can be separated from the body reflection component of the first image by using a spectrum analysis technology. The following provides a possible implementation of separating the melanin and the hemoglobin.

Based on the first spectral response curve of the melanin shown in FIG. 6 and the second spectral response curve of the device having the RGB image photographing function, a first function relationship between the first spectral response curve of the melanin and the second spectral response curve of the device having the RGB image photographing function may be determined. Then, based on channel values of an R channel, a G channel, and a B channel of the device having the RGB image photographing function and the first function relationship, a correspondence between the melanin and the channel values of the three channels, namely the R channel, the G channel, and the B channel, may be determined. For example, the correspondence is represented by the following formula (1):

$$M=g(R,G,B) \quad (1)$$

In the foregoing formula (1), R, G, and B respectively represent channel values of three channels, namely an R channel, a G channel, and a B channel, of an RGB image, and M is a melanin value of the melanin, g is a mapping function from the channel values of the three channels, namely the R channel, the G channel, and the B channel, to the melanin value M.

Figure 5A:
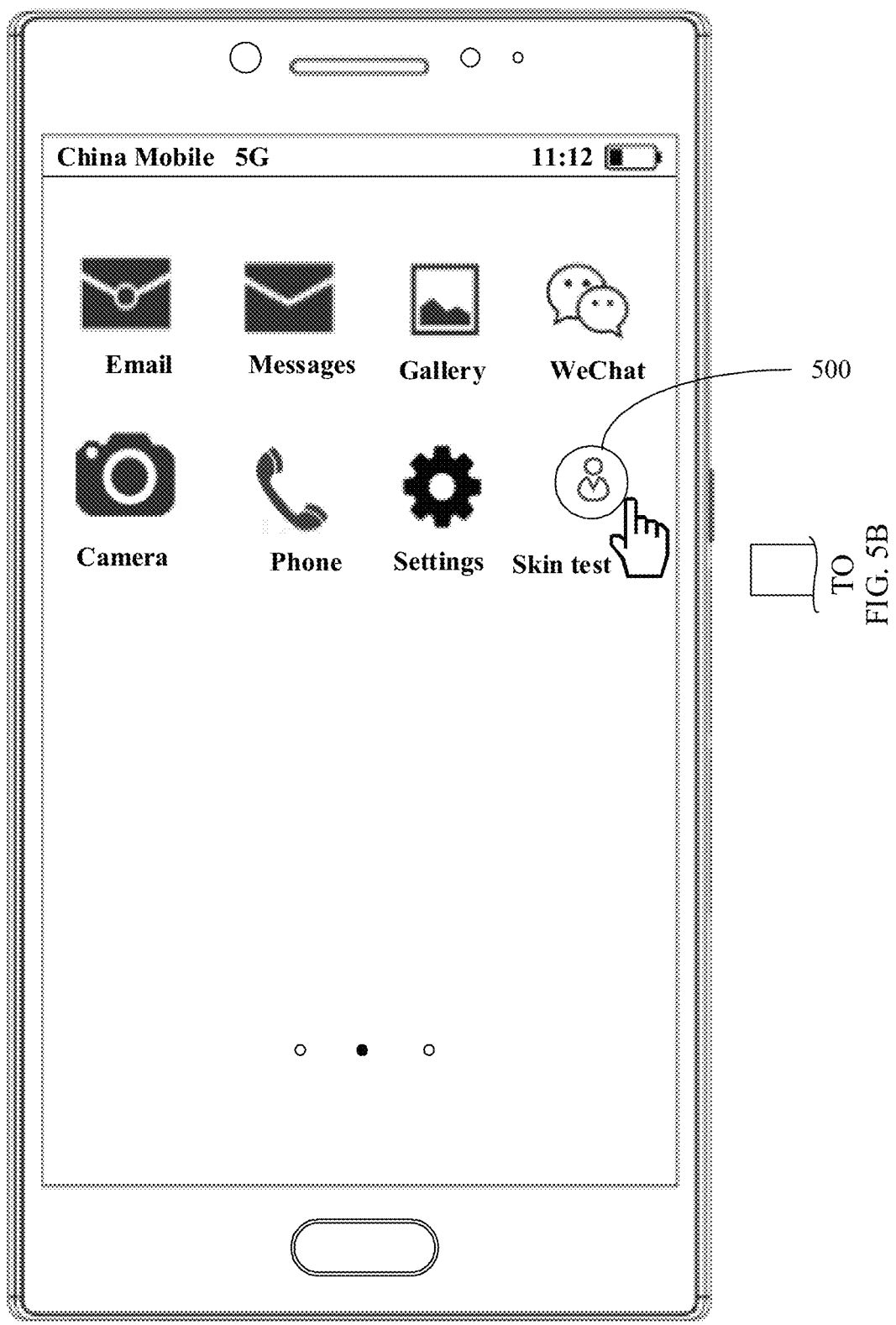
FIG. 5A to FIG. 5D are a schematic diagram of a user interface according to an embodiment of this application.
Figure 5B:
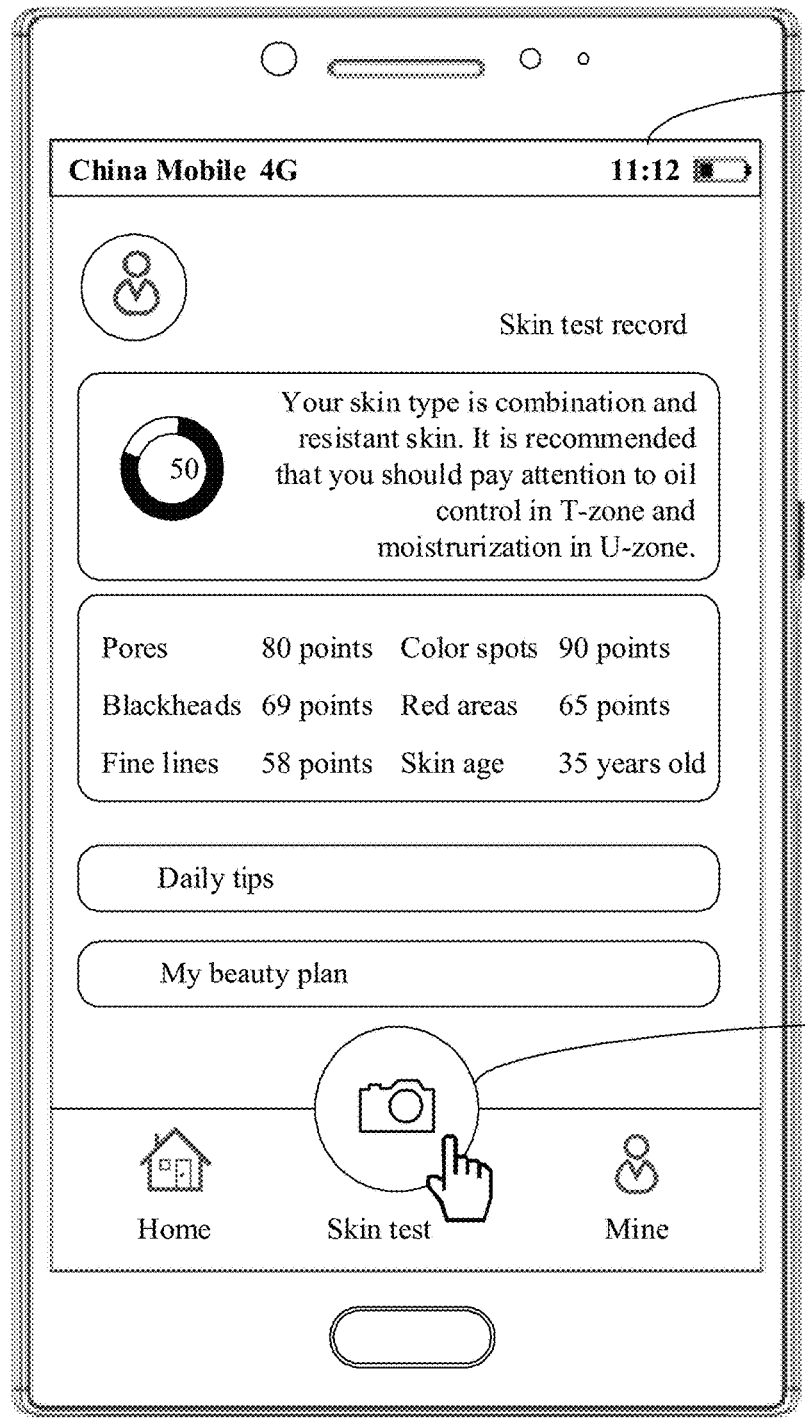
Figure 5C:
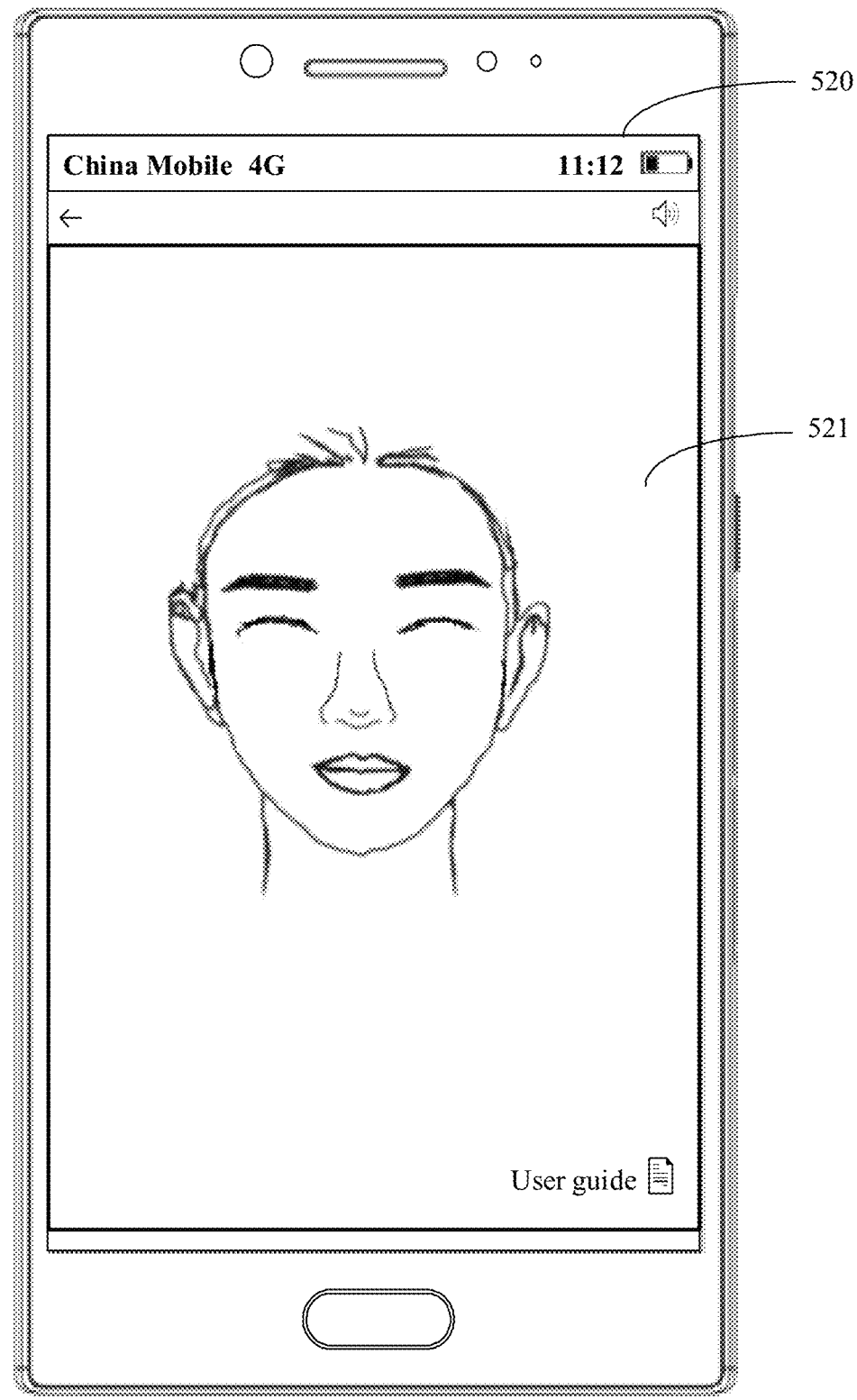
Figure 5D:
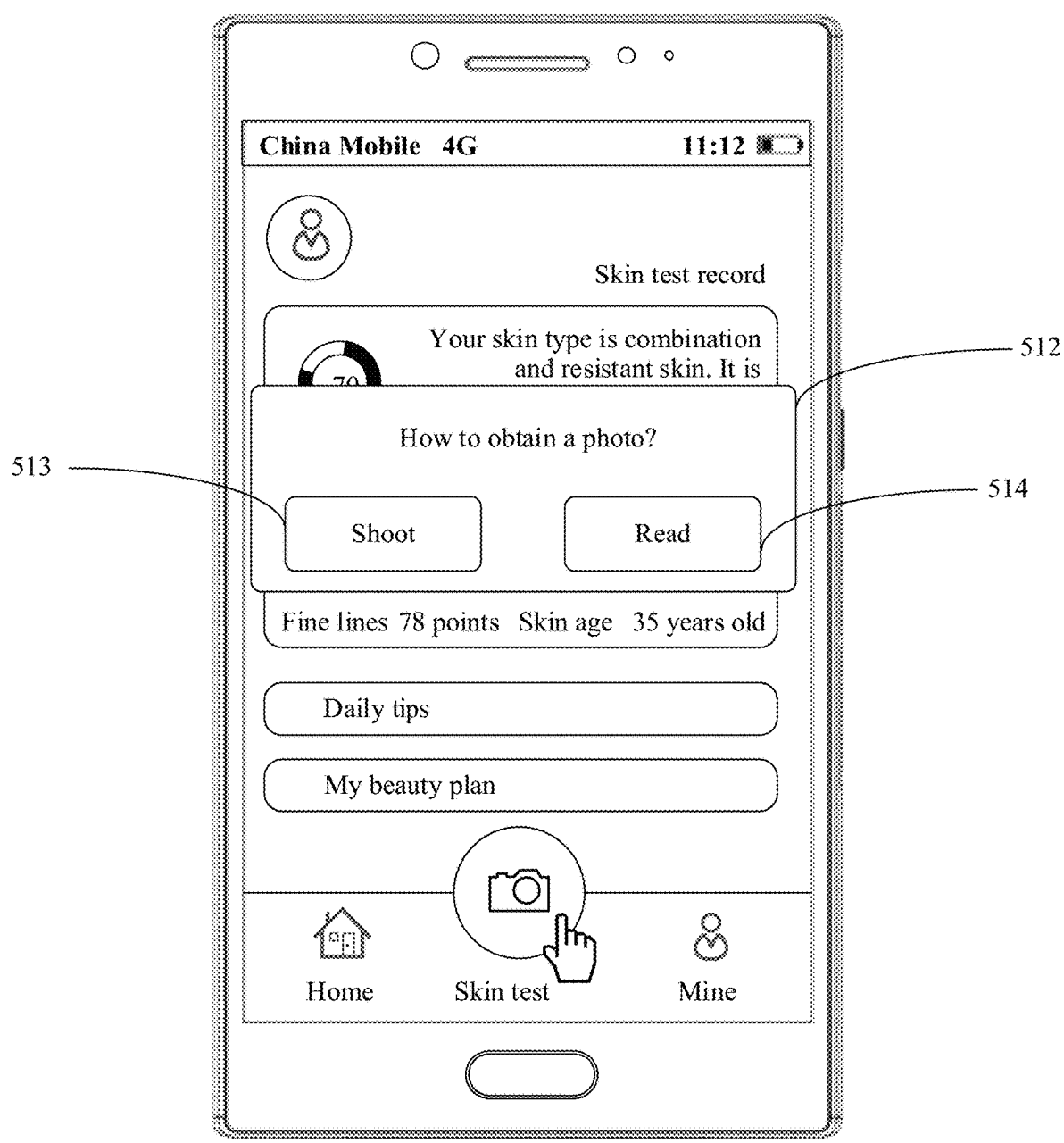
Figure 7:
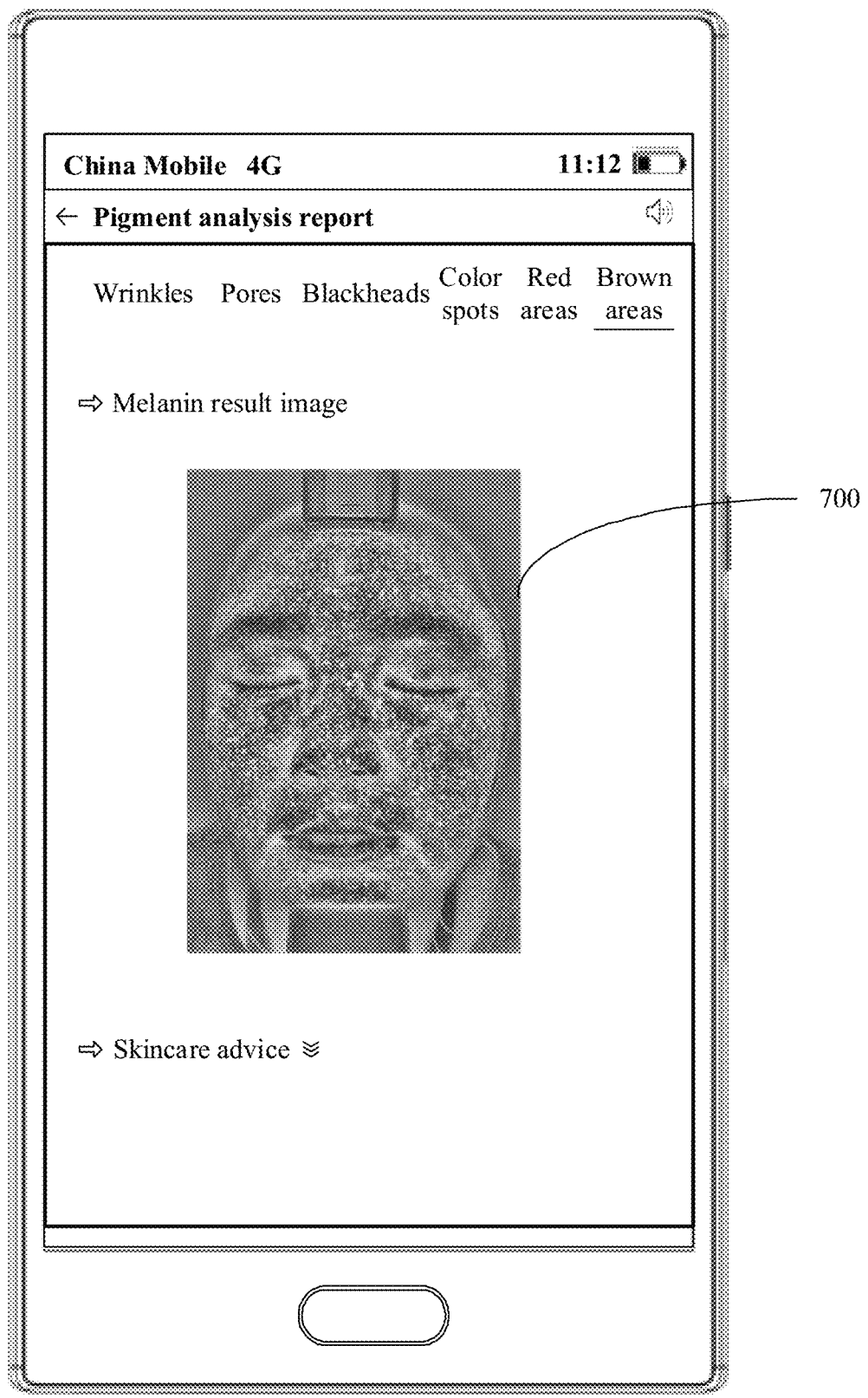
FIG. 7 is a schematic diagram of a grayscale image corresponding to melanin according to an embodiment of this application.

Based on the foregoing formula (1) and a first image extracted from an RGB skin image displayed in the preview area 521 shown in FIG. 5C, the melanin may be extracted from the first image based on channel values of three channels, namely an R channel, a G channel, and a B channel, of the first image. In this way, a grayscale image corresponding to the melanin shown in FIG. 7 can be obtained.

Similarly, based on the first spectral response curve of the hemoglobin shown in FIG. 6 and the second spectral response curve of the device having the RGB image photographing function, a second function relationship between the first spectral response curve of the hemoglobin and the second spectral response curve of the device having the RGB image photographing function may be determined. Then, based on the channel values of the R channel, the G channel, and the B channel of the device having the RGB image photographing function and the second function relationship, a correspondence between the hemoglobin and the channel values of the three channels, namely the R channel, the G channel, and the B channel, may be determined. For example, the correspondence is represented by the following formula (2):

$$H=f(R,G,B) \quad (2)$$

In the foregoing formula (2), R, G, and B respectively represent channel values of three channels, namely an R channel, a G channel, and a B channel, of an RGB image, and H is a hemoglobin value of the hemoglobin, and f is a mapping function from the channel values of the three channels, namely the R channel, the G channel, and the B channel, to the hemoglobin value H.

Figure 8:
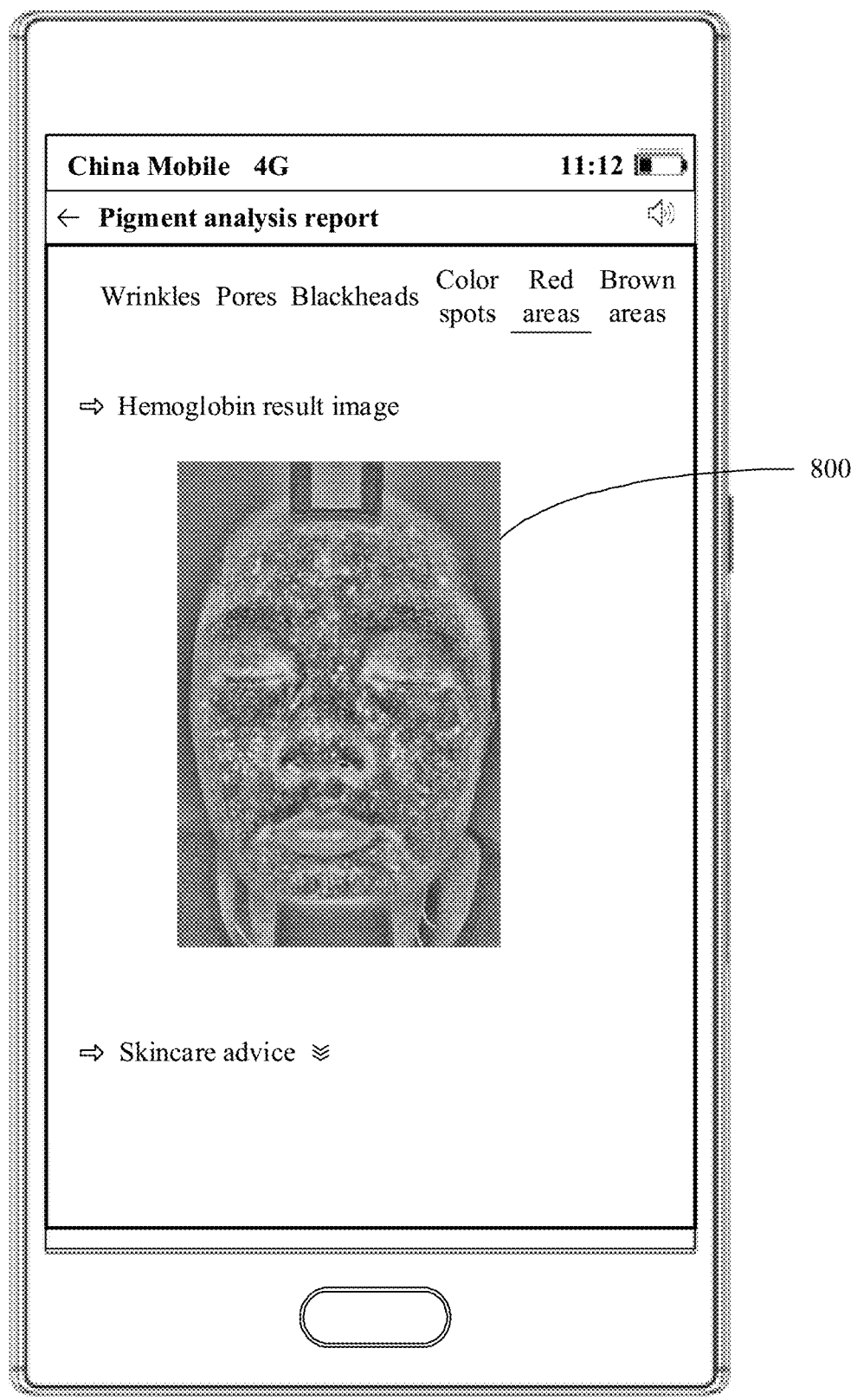
FIG. 8 is a schematic diagram of a grayscale image corresponding to hemoglobin according to an embodiment of this application.

Based on the foregoing formula (2) and the first image extracted from the RGB skin image displayed in the preview area 521 shown in FIG. 5C, the hemoglobin may be extracted from the first image based on the channel values of the three channels, namely the R channel, the G channel, and the B channel, of the first image. In this way, a grayscale image corresponding to the hemoglobin shown in FIG. 8 can be obtained.

It should be noted that the foregoing formula (1) and formula (2) may be mathematical models provided in existing research, or may be models obtained through training by using a machine learning algorithm.

Step 303. The processor 110 generates a pseudo-color image based on the extracted pigment, and displays the pseudo-color image.

In a specific example, the processor 110 generates a grayscale image (a melanin result image shown in FIG. 7 and a hemoglobin result image shown in FIG. 8) based on the extracted pigment, and then converts the grayscale image into a pseudo-color image. In this way, an intuitive pigment detection result can be presented to the user, so that the user can obtain more information from the pseudo-color image.

Specifically, the pseudo-color image may be obtained through mapping by using a preset color lookup table. For example, the color lookup table may include a mapping relationship between different grayscale values and R values, G values, and B values. In this way, a pseudo-color image can be obtained by searching for an R value, a G value, and a B value that are corresponding to a grayscale value of each pixel in the grayscale image.

Further, to obtain a more accurate pigment detection result, the processor 110 may perform post-processing such as normalization processing and contrast enhancement processing on the generated grayscale image, and then convert the post-processed grayscale image into the pseudo-color image.

According to the foregoing solution, the processor 110 extracts the first image from the to-be-detected RGB skin image, where the first image is used to represent the body reflection component in the RGB skin image, and the RGB skin image is photographed by the device having the RGB image photographing function; and the processor 110 extracts the pigment from the first image based on the relationship between the first spectral response curve of the pigment and the second spectral response curve of the device having the RGB image photographing function. In this way, the processor 110 extracts the pigment based on the spectral response relationship, so that pigments in RGB skin images photographed in different scenarios can be detected, avoiding a case in the prior art in which pigment detection can be performed only after training is performed in advance by using skin images acquired in different scenarios. Therefore, pigment detection based on this solution has relatively good applicability.

Based on the foregoing embodiment, to improve fidelity of the first image extracted from the RGB skin image, the following provides an optional implementation, and step 301 is implemented by using steps S1 to S3 below.

S1. The processor 110 converts the to-be-detected RGB skin image into a first Lab image.

Specifically, the processor 110 converts the to-be-detected RGB skin image from RGB color space into Lab color space, to obtain the first Lab image. The conversion from the RGB color space to the Lab color space can be performed by using an algorithm disclosed in the industry.

The RGB color space includes three channels, namely an R channel, a G channel, and a B channel. A color of each pixel in the to-be-detected RGB skin image includes an R value, a G value, and a B value, R values of all the pixels form the R channel, G values of all the pixels form the G channel, and B values of all the pixels form the B channel.

The lab color space includes three channels, namely an L channel, an a channel, and a b channel. L represents pixel luminance, and is unrelated to color information. a and b are related to a color of a pixel, and are unrelated to the pixel luminance. a represents a range from magenta to green, and b represents a range from yellow to blue. A color of each pixel in the first Lab image includes an L value, an a value, and a b value. L values of all the pixels in the first Lab image form the L channel, a values of all the pixels form the a channel, and b values of all the pixels form the b channel.

If filtering processing is performed on the R channel, the G channel, and the B channel of the RGB skin image, color overlapping may occur in a filtering result. As a result, fidelity of an obtained image is poor. The to-be-detected RGB skin image is converted into the first Lab image, so that color-related information and color-unrelated information can be separated, to separately process the color-related information in the first Lab image.

S2. The processor 110 extracts a body reflection component from each of the L channel, the a channel, and the b channel of the first Lab image.

For example, the processor 110 may separately perform filtering processing on the L channel, the a channel, and the b channel of the first Lab image, to obtain the body reflection components of the L channel, the a channel, and the b channel of the first Lab image.

An initial value of each of the L channel, the a channel, and the b channel of the first Lab image includes a body reflection component and a surface reflection component. In an implementation, filtering processing is separately performed on the initial values of the L channel, the a channel, and the b channel of the first Lab image to obtain surface reflection components of the L channel, the a channel, and the b channel of the first Lab image, and then body reflection components of the L channel, the a channel, and the b channel are determined. The body reflection component of the L channel of the first Lab image is a difference between an initial value of the L channel of the first Lab image and a surface reflection component of the L channel of the first Lab image; the body reflection component of the a channel of the first Lab image is a difference between an initial value of the a channel of the first Lab image and a surface reflection component of the a channel of the first Lab image; and the body reflection component of the b channel of the first Lab image is a difference between an initial value of the b channel of the first Lab image and a surface reflection component of the b channel of the first Lab image. In this way, the surface reflection components of the L channel, the a channel, and the b channel may be filtered out, to accurately extract the body reflection components from the L channel, the a channel, and the b channel.

Further, to improve pigment detection accuracy, the surface reflection components of all the L channel, the a channel, and the b channel of the first Lab image are obtained by separately performing bilateral filtering processing on the initial values of the L channel, the a channel, and the b channel of the first Lab image. This solution can help further retain edge information of the first image, thereby improving the pigment detection accuracy.

S3. The processor 110 combines the body reflection components extracted from the L channel, the a channel, and the b channel of the first Lab image to obtain a second Lab image.

S4. The processor 110 converts the second Lab image into an RGB image to obtain the first image.

Specifically, the processor 110 converts the second Lab image from the Lab color space into the RGB color space, to obtain the first image. The conversion from the Lab color space to the RGB color space can be performed by using an algorithm disclosed in the industry.

According to steps S1 to S4, the color-related information and the color-unrelated information can be separately processed, thereby helping improve the fidelity of the first image.

It should be understood that the foregoing embodiments of this application may be used in combination, or may be separately used.

In the foregoing embodiments provided in this application, the method provided in the embodiments of this application is described from a perspective of the electronic device serving as an execution body. To implement the functions in the method provided in the embodiments of this application, the electronic device may include a hardware structure and/or a software module, and implement the functions in a form of the hardware structure, the software module, or a combination of the hardware structure and the software module. Whether a function in the foregoing functions is performed by the hardware structure, the software module, or the combination of the hardware structure and the software module depends on a particular application and a design constraint of the technical solution.

Figure 9:
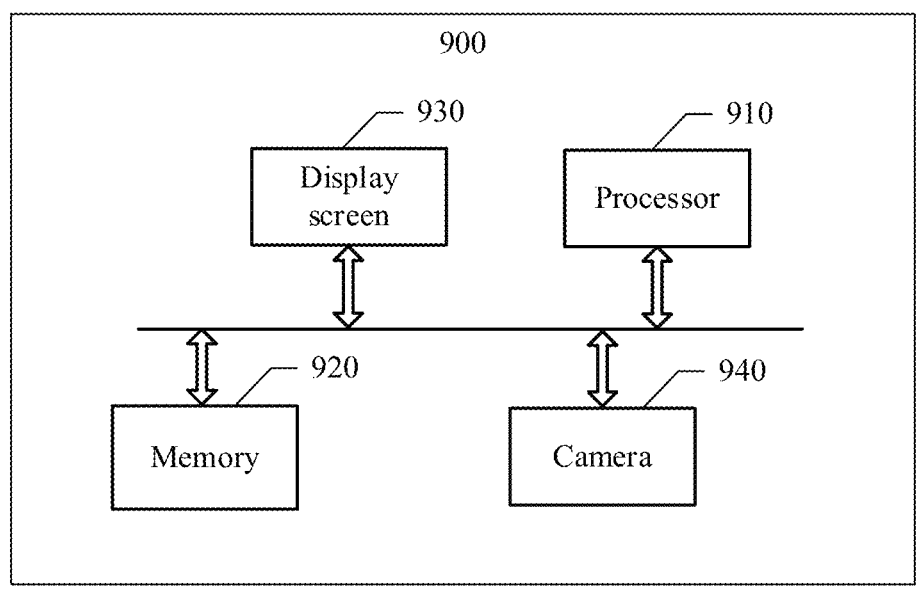
FIG. 9 is a schematic diagram of a structure of an electronic device to which an embodiment of this application is applicable.

Based on a same concept, FIG. 9 shows an electronic device 900 according to this application. For example, the electronic device 900 includes at least one processor 910, a memory 920, and a display screen 930, and may further include the display screen 930 and a camera 940. The processor 910 is coupled to the memory 920, the display screen 930, and the camera 940. The coupling in this embodiment of this application is an indirect coupling or a communication connection between apparatuses, units, or modules, may be in an electrical form, a mechanical form, or another form, and is used for information exchange between the apparatuses, units, or modules.

Specifically, the memory 920 is configured to store a program instruction.

Figure 3:
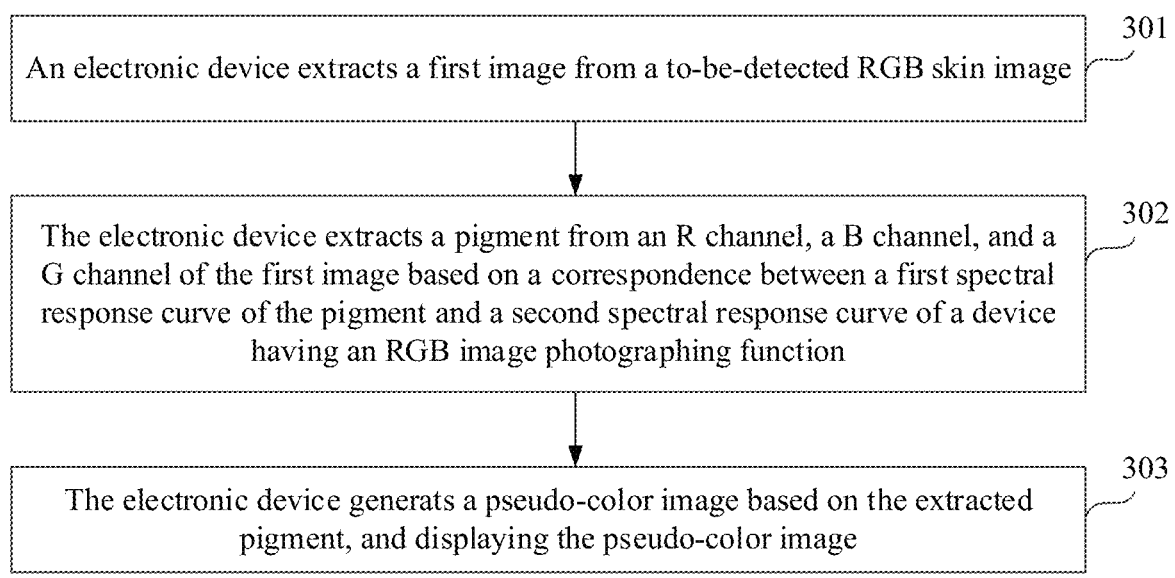
FIG. 3 is a schematic flowchart of a pigment detection method according to an embodiment of this application.

The processor 910 is configured to invoke the program instruction stored in the memory 920, so that the electronic device 900 performs the steps performed by the electronic device in the pigment detection method shown in FIG. 3.

The display screen 930 is configured to display a pigment detection result obtained by the processor 910, for example, display the pseudo-color image in step 303. The display screen may further be configured to display a preview interface when the camera 940 starts photographing, where the preview interface includes an image acquired by the camera 940, and is used to display the user interface designed in the foregoing embodiment.

It should be understood that the electronic device 900 may be configured to implement the pigment detection method shown in FIG. 3 in the embodiments of this application. For related features, refer to the foregoing descriptions. Details are not described herein again.

A person skilled in the art may clearly know that the embodiments of this application may be implemented by using hardware, firmware, or a combination thereof. When the present invention is implemented by software, the foregoing functions may be stored in a computer-readable medium or transmitted as one or more instructions or code in the computer-readable medium. The computer-readable medium includes a computer storage medium and a communications medium, where the communications medium includes any medium that enables a computer program to be transmitted from one place to another. The storage medium may be any available medium accessible to a computer. By way of example and not limitation, a computer-readable medium may include a RAM, a ROM, an electrically erasable programmable read only memory (EEPROM), a compact disc read-only memory (CD-ROM) or another optical disc storage, a magnetic disk storage medium or another magnetic storage device, or any other computer-accessible medium that can be used to carry or store expected program code in an instruction or data structure form. In addition, any connection may be appropriately defined as a computer-readable medium. For example, if software is transmitted from a website, a server or another remote source by using a coaxial cable, an optical fiber/cable, a twisted pair, a digital subscriber line (DSL) or wireless technologies such as infrared ray, radio and microwave, the coaxial cable, optical fiber/cable, twisted pair, DSL or wireless technologies such as infrared ray, radio and microwave are included in fixation of a medium to which they belong. A disk and disc used by the embodiments of this application includes a compact disc (CD), a laser disc, an optical disc, a digital video disc (DVD), a floppy disk and a Blu-ray disc, where the disk generally copies data by a magnetic means, and the disc copies data optically by a laser means. The foregoing combination should also be included in the protection scope of the computer-readable medium.

In summary, what is described above is merely embodiments of this application, but is not intended to limit the protection scope of this application. Any modification, equivalent replacement, improvement, or the like made according to the disclosure of this application shall fall within the protection scope of this application.

What is claimed is:

1. A pigment detection method, comprising:
   extracting a first image from an RGB skin image, wherein the first image is used to represent a body reflection component in the RGB skin image, and the RGB skin image is photographed by a device having an RGB image photography function;
   extracting a pigment from an R channel, a B channel, and a G channel of the first image by determining a function relationship between a first spectral response curve of the pigment and a second spectral response curve of photosensitive units in the device, and by determining a correspondence between the pigment and channel values of the R channel, G channel, and B channel;
   generating a pseudo-color image based on the extracted pigment; and
   displaying the pseudo-color image.

2. The method of claim 1, wherein the method further comprises:
   converting the RGB skin image into a first Lab image;
   extracting a body reflection component from each of an L channel, an a channel, and a b channel of the first Lab image;
   combining the body reflection components extracted from the L channel, the a channel, and the b channel of the first Lab image to obtain a second Lab image; and
   converting the second Lab image into an RGB image to obtain the first image.

3. The method of claim 2, wherein the body reflection component of the L channel of the first Lab image is a difference between an initial value of the L channel of the first Lab image and a surface reflection component of the L channel of the first Lab image; the body reflection component of the a channel of the first Lab image is a difference between an initial value of the a channel of the first Lab image and a surface reflection component of the a channel of the first Lab image; and the body reflection component of the b channel of the first Lab image is a difference between an initial value of the b channel of the first Lab image and a surface reflection component of the b channel of the first Lab image, wherein
   the surface reflection components of the L channel, the a channel, and the b channel of the first Lab image are obtained by separately performing filtering processing on the initial values of the L channel, the a channel, and the b channel of the first Lab image.

4. The method of claim 3, wherein the surface reflection components of the L channel, the a channel, and the b channel of the first Lab image are obtained by performing bilateral filtering processing on the initial values of the L channel, the a channel, and the b channel of the first Lab image.

5. The method of claim 1, wherein the pigment comprises hemoglobin.

6. The method of claim 1, wherein the pigment comprises melanin.

7. The method of claim 1, wherein the pigment comprises carotene.

8. The method of claim 1, wherein the pigment comprises lipochrome.

9. The method of claim 1, wherein the pigment comprises bile pigment.

10. An electronic device, comprising:
    a memory comprising instructions; and
    a processor coupled to the memory, the instructions being executed by the processor to cause the electronic device to:
    extract a first image from an RGB skin image, wherein the first image is used to represent a body reflection component in the RGB skin image, and the RGB skin image is photographed by a device having an RGB image photography function;
    extract a pigment from an R channel, a B channel, and a G channel of the first image by determining a function relationship between a first spectral response curve of the pigment and a second spectral response curve of photosensitive units in the device, and by determining a correspondence between the pigment and channel values of the R channel, G channel, and B channel;
    generate a pseudo-color image based on the extracted pigment; and
    display the pseudo-color image.

11. The electronic device of claim 10, wherein the instructions further cause the electronic device to:
    convert the RGB skin image into a first Lab image;
    extract a body reflection component from each of an L channel, an a channel, and a b channel of the first Lab image;
    combine the body reflection components extracted from the L channel, the a channel, and the b channel of the first Lab image to obtain a second Lab image; and
    convert the second Lab image into an RGB image to obtain the first image.

12. The electronic device of claim 11, wherein the body reflection component of the L channel of the first Lab image is a difference between an initial value of the L channel of the first Lab image and a surface reflection component of the L channel of the first Lab image; the body reflection component of the a channel of the first Lab image is a difference between an initial value of the a channel of the first Lab image and a surface reflection component of the a channel of the first Lab image; and the body reflection component of the b channel of the first Lab image is a difference between an initial value of the b channel of the first Lab image and a surface reflection component of the b channel of the first Lab image.

13. The electronic device of claim 12, wherein the surface reflection components of the L channel, the a channel, and the b channel of the first Lab image are obtained by separately performing filtering processing on the initial values of the L channel, the a channel, and the b channel of the first Lab image.

14. The electronic device of claim 12, wherein the surface reflection components of the L channel, the a channel, and the b channel of the first Lab image are obtained by performing bilateral filtering processing on the initial values of the L channel, the a channel, and the b channel of the first Lab image.

15. A computer program product for detecting a pigment, the computer program product being embodied in a non-transitory computer readable medium and comprising computer instructions for:
    extracting a first image from an RGB skin image, wherein the first image is used to represent a body reflection component in the RGB skin image, and the RGB skin image is photographed by a device having an RGB image photography function;

extracting a pigment from an R channel, a B channel, and a G channel of the first image by determining a function relationship between a first spectral response curve of the pigment and a second spectral response curve of photosensitive units in the device, and by determining a correspondence between the pigment and channel values of the R channel, G channel, and B channel;

generating a pseudo-color image based on the extracted pigment; and displaying the pseudo-color image.

16. The computer program product of claim 15, wherein the computer program product further comprises computer instructions for:

converting the RGB skin image into a first Lab image;

extracting a body reflection component from each of an L channel, an a channel, and a b channel of the first Lab image;

combining the body reflection components extracted from the L channel, the a channel, and the b channel of the first Lab image to obtain a second Lab image; and converting the second Lab image into an RGB image to obtain the first image.

17. The computer program product of claim 16, wherein the body reflection component of the L channel of the first Lab image is a difference between an initial value of the L channel of the first Lab image and a surface reflection component of the L channel of the first Lab image; the body reflection component of the a channel of the first Lab image is a difference between an initial value of the a channel of the first Lab image and a surface reflection component of the a channel of the first Lab image; and the body reflection component of the b channel of the first Lab image is a difference between an initial value of the b channel of the first Lab image and a surface reflection component of the b channel of the first Lab image.

18. The computer program product of claim 17, wherein the surface reflection components of the L channel, the a channel, and the b channel of the first Lab image are obtained by separately performing filtering processing on the initial values of the L channel, the a channel, and the b channel of the first Lab image.

19. The computer program product of claim 17, wherein the surface reflection components of the L channel, the a channel, and the b channel of the first Lab image are obtained by performing bilateral filtering processing on the initial values of the L channel, the a channel, and the b channel of the first Lab image.

20. The computer program product of claim 15, wherein the pigment comprises hemoglobin.

* * * * *